(12) United States Patent
Lin et al.

(10) Patent No.: US 9,901,928 B2
(45) Date of Patent: Feb. 27, 2018

(54) CALIBRATION FLUID CARTRIDGE FOR AN IN VITRO MEDICAL DIAGNOSTIC DEVICE

(71) Applicant: Edan Diagnostics, San Diego, CA (US)

(72) Inventors: Chao Lin, San Diego, CA (US); Paul Swanson, Santee, CA (US); Zhixiang Jason Zhao, Plainsboro, NJ (US)

(73) Assignee: EDAN DIAGNOSTICS, San Diego, CA (US)

( * ) Notice: Subject to any disclaimer, the term of this patent is extended or adjusted under 35 U.S.C. 154(b) by 42 days.

(21) Appl. No.: 13/707,517

(22) Filed: Dec. 6, 2012

(65) Prior Publication Data
US 2013/0142709 A1 Jun. 6, 2013

Related U.S. Application Data

(60) Provisional application No. 61/567,585, filed on Dec. 6, 2011, provisional application No. 61/725,476, filed on Nov. 12, 2012.

(51) Int. Cl.
B01L 3/00 (2006.01)
F16K 99/00 (2006.01)
G01N 27/26 (2006.01)
G01N 27/327 (2006.01)
G01N 27/416 (2006.01)
G01N 33/49 (2006.01)

(52) U.S. Cl.
CPC ......... B01L 3/567 (2013.01); B01L 3/502715 (2013.01); B01L 3/502738 (2013.01); F16K 99/0015 (2013.01); F16K 99/0026 (2013.01); G01N 27/26 (2013.01); G01N 27/3273 (2013.01); G01N 27/4163 (2013.01); G01N 33/492 (2013.01); B01L 2200/027 (2013.01); B01L 2200/0673 (2013.01); B01L 2200/148 (2013.01); B01L 2300/0645 (2013.01); B01L 2300/0816 (2013.01); B01L 2300/0838 (2013.01); B01L 2300/0867 (2013.01); B01L 2300/0883 (2013.01); B01L 2300/1805 (2013.01); B01L 2400/0487 (2013.01); B01L 2400/0655 (2013.01); F16K 2099/0084 (2013.01)

(58) Field of Classification Search
CPC ........... G01N 27/4163; B01L 2300/087; B01L 2200/027; B01L 3/567; B01L 2200/16
USPC ........ 422/68.1, 81, 500, 537, 538, 543, 554; 436/43, 180; 204/403.2
See application file for complete search history.

(56) References Cited

U.S. PATENT DOCUMENTS

D239,881 S    5/1976  Morgan et al.
4,341,538 A   7/1982  Vadnay et al.
D267,037 S    11/1982 Spranger et al.
(Continued)

OTHER PUBLICATIONS

Non-Final Office Action dated Jan. 14, 2014, as received in co-pending Design U.S. Appl. No. 29/437,043.
(Continued)

Primary Examiner — Dennis M White
Assistant Examiner — Bryan Kilpatrick
(74) Attorney, Agent, or Firm — Gilberto M. Villacorta; Brett P. Belden; Foley & Lardner LLP

(57) ABSTRACT

The present disclosure relates to a calibration cartridge for an in vitro medical diagnostic device. The device also includes a removable assay cartridge containing a polymer body with channels for fluid movement.

13 Claims, 38 Drawing Sheets

(56) References Cited

U.S. PATENT DOCUMENTS

| | | | |
|---|---|---|---|
| D282,282 S | 1/1986 | Chernack | |
| D288,478 S | 2/1987 | Carlson et al. | |
| D307,324 S | 4/1990 | Unger et al. | |
| D312,695 S | 12/1990 | Unger et al. | |
| D314,435 S | 2/1991 | Unger et al. | |
| D319,504 S | 8/1991 | Sone et al. | |
| 5,042,691 A | 8/1991 | Maldonado | |
| D322,124 S | 12/1991 | Lichte et al. | |
| 5,078,361 A * | 1/1992 | Nordman | F16K 7/045 251/129.01 |
| D328,789 S | 8/1992 | Kopf | |
| D336,514 S | 6/1993 | Valerio et al. | |
| D390,661 S | 2/1998 | Foggia | |
| D404,140 S | 1/1999 | Meguro | |
| D445,509 S | 7/2001 | Berndt et al. | |
| D447,569 S | 9/2001 | Baily et al. | |
| D451,602 S | 12/2001 | Juhlin et al. | |
| D467,349 S | 12/2002 | Niedbala et al. | |
| D475,787 S | 6/2003 | Zia et al. | |
| D489,816 S | 5/2004 | Ross | |
| D516,221 S | 2/2006 | Wohlstadter et al. | |
| D597,216 S | 7/2009 | McGuigan et al. | |
| D623,300 S | 9/2010 | Zimerman et al. | |
| D634,442 S | 3/2011 | Tajima et al. | |
| D638,545 S | 5/2011 | Okawa et al. | |
| D647,209 S | 10/2011 | Muller et al. | |
| D657,067 S | 4/2012 | Shibata | |
| D665,917 S | 8/2012 | TerMaat et al. | |
| D675,335 S | 1/2013 | Feuerabend et al. | |
| D681,231 S | 4/2013 | Steinhauer et al. | |
| D694,422 S | 11/2013 | Cook et al. | |
| D705,943 S | 5/2014 | Chang et al. | |
| D706,930 S | 6/2014 | Lin et al. | |
| 8,741,234 B2 | 6/2014 | Wang et al. | |
| 8,741,235 B2 | 6/2014 | Janisch et al. | |
| D708,749 S | 7/2014 | Appling et al. | |
| 2003/0057108 A1 | 3/2003 | Sridharan | |
| 2003/0073089 A1 | 4/2003 | Mauze et al. | |
| 2005/0148091 A1* | 7/2005 | Kitaguchi et al. | 436/164 |
| 2006/0127275 A1* | 6/2006 | Holl et al. | 422/57 |
| 2007/0059204 A1 | 3/2007 | Witty et al. | |
| 2007/0172388 A1 | 7/2007 | Padmanabhan et al. | |
| 2007/0292941 A1* | 12/2007 | Handique | B01L 3/5027 435/288.7 |
| 2008/0153096 A1 | 6/2008 | Witty et al. | |
| 2009/0065368 A1 | 3/2009 | Davis et al. | |
| 2010/0273248 A1 | 10/2010 | Ha et al. | |
| 2010/0328405 A1 | 12/2010 | Ness et al. | |
| 2011/0086378 A1 | 4/2011 | Shany et al. | |
| 2011/0198241 A1 | 8/2011 | Murakami | |
| 2011/0229373 A1 | 9/2011 | Asakura | |
| 2011/0287447 A1 | 11/2011 | Norderhaug et al. | |
| 2012/0179101 A1 | 7/2012 | Briones et al. | |
| 2012/0193376 A1 | 8/2012 | Evans et al. | |
| 2012/0218740 A1 | 8/2012 | Estes et al. | |
| 2013/0140177 A1 | 6/2013 | Lin et al. | |
| 2013/0140179 A1 | 6/2013 | Lin et al. | |

OTHER PUBLICATIONS

Notice of Allowance dated Jan. 17, 2014, as received in co-pending Design U.S. Appl. No. 29/437,042.
U.S. Appl. No. 29/437,042, filed Nov. 12, 2012, Lin et al.
U.S. Appl. No. 29/437,043, filed Nov. 12, 2012, Lin et al.
U.S. Appl. No. 29/437,044, filed Nov. 12, 2012, Lin et al.
Search Report and Written Opinion for Int'l Appln No. PCT/US2012/068299 dated Apr. 1, 2013.
US Office Action on 104218-0200 dated Jun. 5, 2013.
US Office Action on 104218-0300 dated Jun. 5, 2013.
Office Action issued in related U.S. Appl. No. 29/437,044, dated May 21, 2014.
Notice of Allowance issued in related U.S. Appl. No. 29/437,043, dated Jul. 2, 2014.
International Preliminary Report on Patentability issued in related International Patent Application No. PCT/US2012/068299, dated Jun. 10, 2014.
Office Action issued in related U.S. Appl. No. 29/504,942, dated Feb. 9, 2015.
US Office Action on 104218-0201 dated Sep. 24, 2014, U.S. Appl. No. 29/491,357.
Notice of Allowance issued in related U.S. Appl. No. 29/437,043, dated Aug. 26, 2014.
Notice of Allowance issued in related U.S. Appl. No. 29/437,044, dated Aug. 11, 2014.
Notice of Allowance issued in related U.S. Appl. No. 13/707,513, dated Nov. 17, 2014.
Office Action issued in related U.S. Appl. No. 13/707,510, dated May 4, 2015.
Notice of Allowance issued in related Design U.S. Appl. No. 29/491,357, dated May 26, 2015.
Notice of Allowance issued in related Design U.S. Appl. No. 29/504,942, dated Jun. 3, 2015.
Notice of Allowance issued in related Design U.S. Appl. No. 29/503,906, dated May 13, 2015.
Notice of Allowance issued in related U.S. Appl. No. 13/707,510, dated Oct. 7, 2015.

* cited by examiner

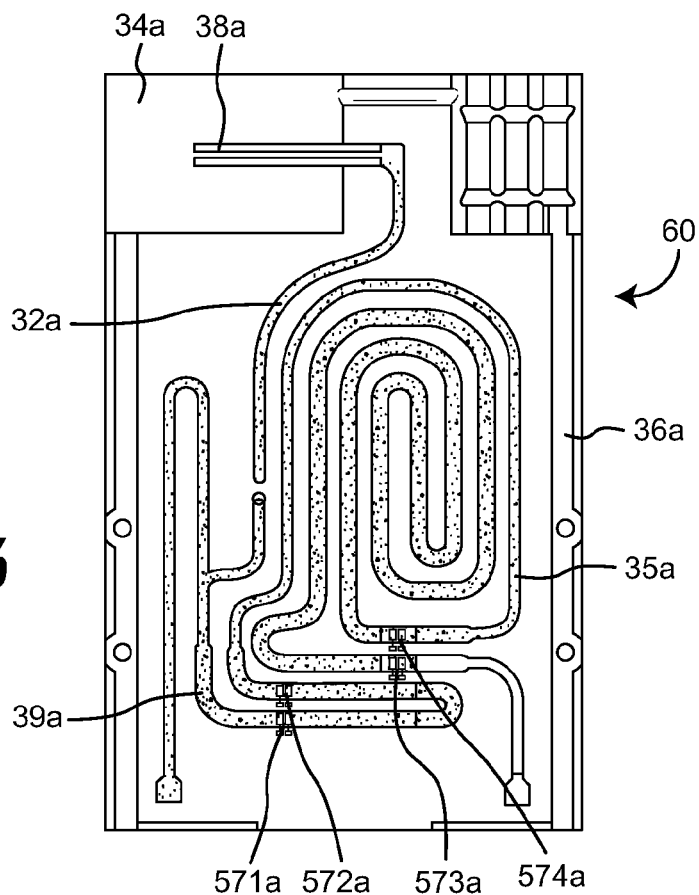
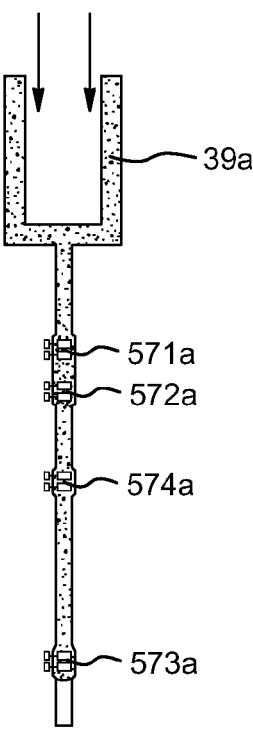
FIG. 16
FIG. 17

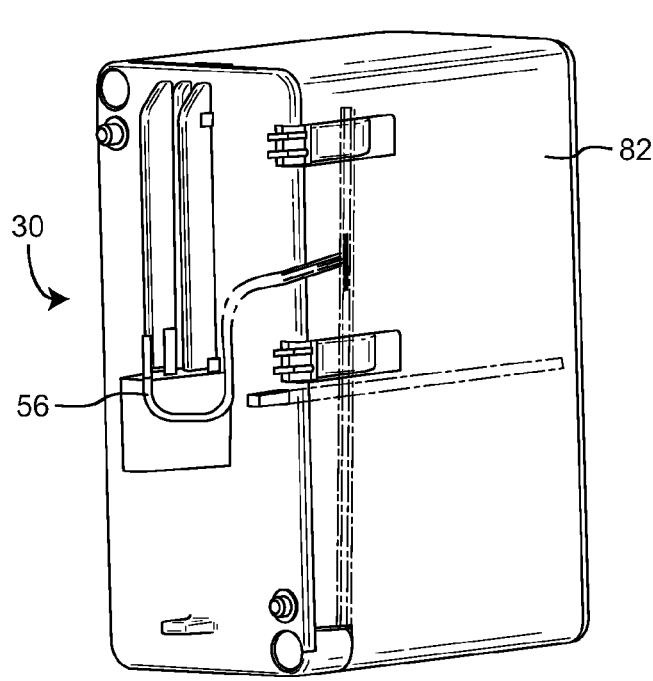
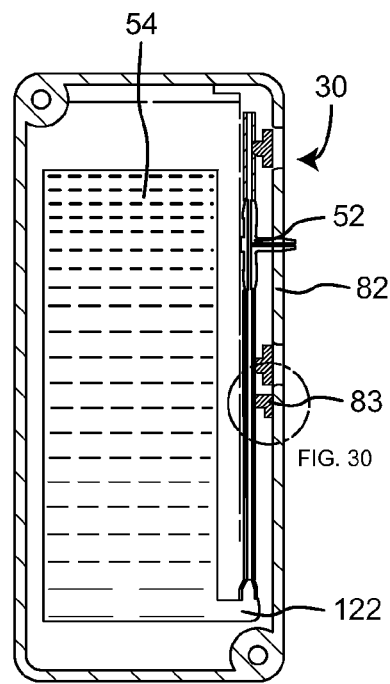
FIG. 28  FIG. 29
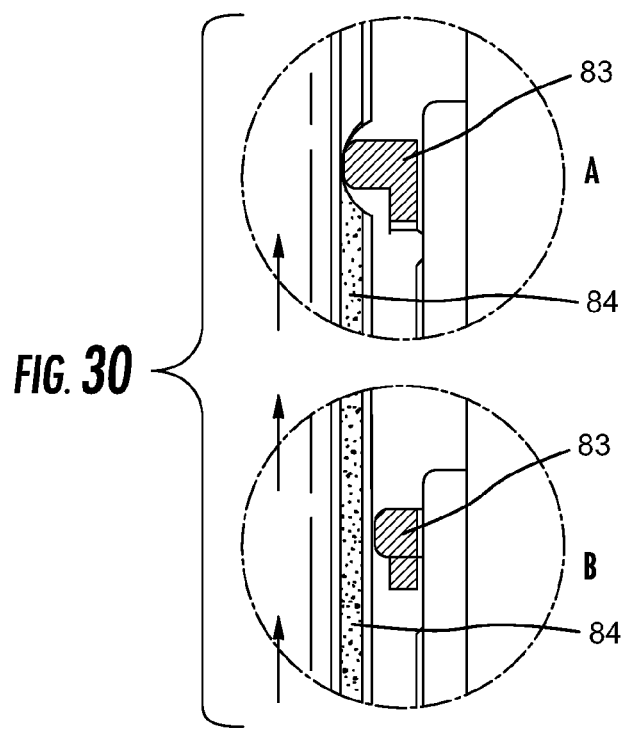
FIG. 30

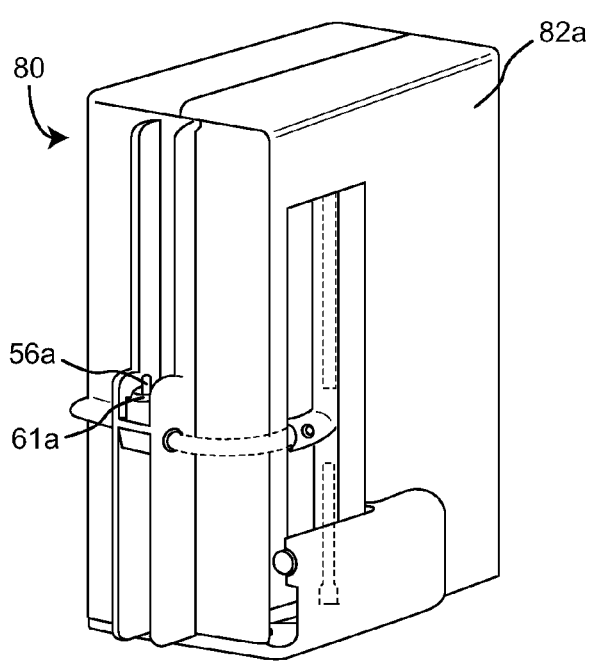
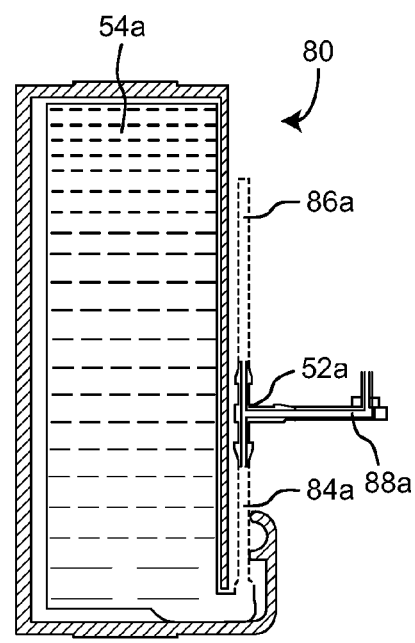
FIG. 35
FIG. 36

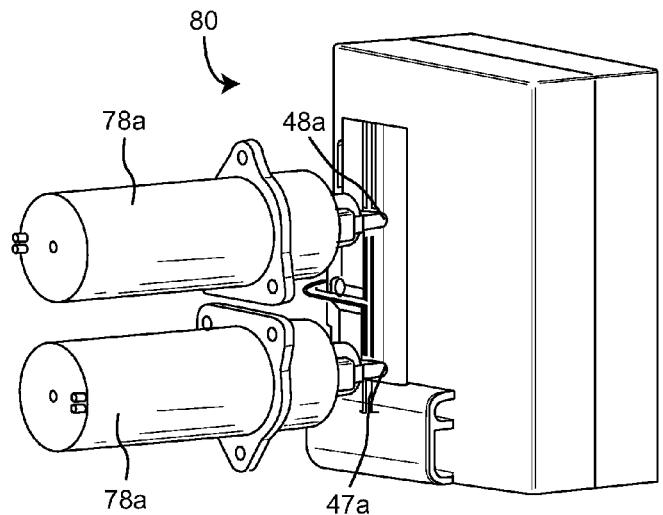
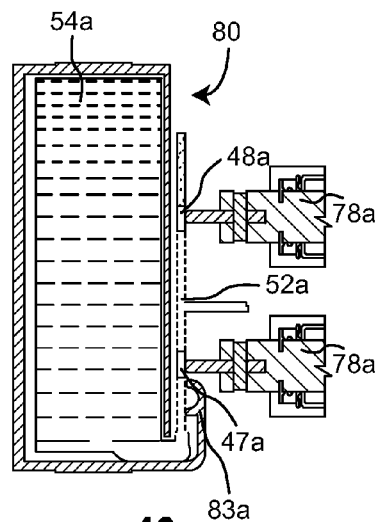
FIG. 39
FIG. 40
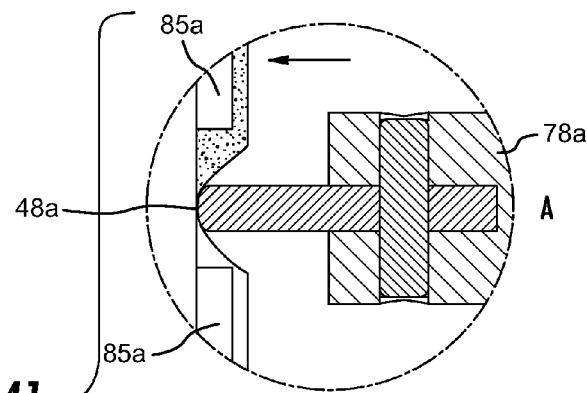
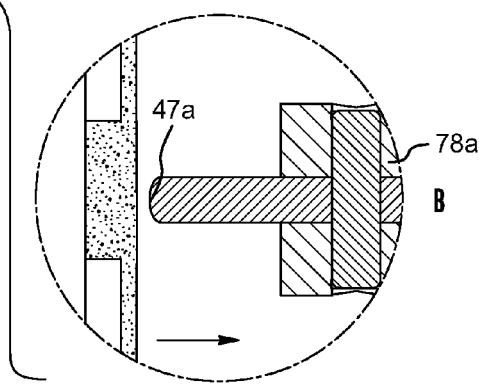
FIG. 41

CALIBRATION FLUID CARTRIDGE FOR AN IN VITRO MEDICAL DIAGNOSTIC DEVICE

CROSS-REFERENCE TO RELATED APPLICATIONS

The present Application claims the benefit of and priority to U.S. Provisional Patent Application No. 61/567,585 titled "Diagnostic Device" and filed on Dec. 6, 2011, the complete disclosure of which is incorporated herein by reference. The present Application also claims the benefit of and priority to U.S. Provisional Patent Application No. 61/725,476, filed Nov. 12, 2012, the entirety of which is incorporated herein by reference.

BACKGROUND

Electrochemical diagnostic devices are analytical tools combining a chemical or biochemical recognition component (e.g., an enzyme or antibody) with a physical transducer such as a platinum electrode. The chemical or biochemical recognition component can be used to selectively interact with an analyte of interest and generate an electrical signal through the transducer. The selectivity of certain biochemical recognition components makes it possible to develop electrochemical sensors which can accurately detect certain biological analytes in blood.

In vitro diagnostic testing has traditionally been performed at large, well-equipped testing centers. These conventional testing centers offer efficient and accurate testing of a high volume of fluid samples, but are not able to offer immediate results. A medical practitioner must collect fluid samples, the samples must be transported to a laboratory, then processed by the laboratory, and finally the results are communicated to the patient. Conventional in vitro diagnostic testing does not offer immediate results.

Also, conventional in vitro diagnostic testing requires trained laboratory technicians to perform the testing in order to ensure the accuracy and reliability of the test. User errors by the person handling the sample can result in contamination of surfaces, spilled specimens, or damage to the diagnostic device resulting in extensive repair and maintenance costs. Conventional in vitro diagnostic testing requires a skilled technician to perform multiple stages of the testing process, and is still subject to user error.

SUMMARY

An embodiment of the present disclosure relates to a diagnostic system. The diagnostic system includes a removable assay cartridge comprising fluid paths and a plurality of electrochemical sensors, a removable calibration fluid cartridge, and a diagnostic device having a housing and processing electronics for conducting the diagnostics within the housing. The housing further includes a first opening for receiving at least a portion of the removable assay cartridge and a second opening for receiving at least a portion of the removable calibration fluid cartridge. The processing electronics of the diagnostic device receive signals from the electrochemical sensors and the removable assay cartridge and the removable calibration fluid cartridge engage for the communication of fluid so that there is no fluid communication from the removable assay cartridge to any surface of the diagnostic device and no fluid communication from the removable calibration fluid cartridge to any surface of the diagnostic device.

In this embodiment, the diagnostic system may include one or more valve control mechanisms. The valve control mechanism includes a cam plate configured to rotate, the cam plate under control of the processing electronics and having one or more concentric grooves comprising one or more raised portions. The valve control mechanism also includes one or more valve actuators having one or more guides, the guides configured to align with the concentric grooves, maintaining contact with the grooves as the cam plate rotates. The valve actuators are configured to actuate one or more valves when the guides encounter the raised portion of the cam plate, and the valves are configured to control at least the flow of fluid in the removable assay cartridge.

Another embodiment of the present disclosure relates to a diagnostic device. The diagnostic device includes a housing having an assay port for receiving a removable assay cartridge, a circuit receiving data from at least one electrochemical sensor on the removable assay cartridge when the removable assay cartridge is fully installed in the assay port, processing electronics configured to receive the data from the circuit and to conduct diagnostics using the received data, and a valve control mechanism under control of the processing electronics and configured to control the flow of fluid in the removable assay cartridge without touching the fluid in the removable assay cartridge.

In this embodiment, the valve control mechanism may include a cam plate configured to rotate, the cam plate under control of the processing electronics and having one or more concentric grooves comprising one or more raised portions. The valve control mechanism may also include one or more valve actuators having one or more guides, the guides configured to align with the concentric grooves, maintaining contact with the grooves as the cam plate rotates. The valve actuators may be configured to actuate one or more valves when the guides encounter the raised portion of the cam plate, and the valves may be configured to control at least the flow of fluid in the removable assay cartridge.

Another embodiment of the present disclosure relates to a valve control mechanism for a diagnostic device configured to receive a removable assay cartridge. The valve control mechanism includes an engagement device having a cycle with one or more predetermined points, the engagement device configured to engage one or more valve actuators at one or more predetermined points of the cycle, one or more valve actuators configured to actuate one or more valves when the valve actuators are engaged by the engagement device. The valves are configured to control at least the flow of fluid in the removable assay cartridge.

Another embodiment of the present disclosure relates to a calibration fluid cartridge for a diagnostic device. The calibration fluid cartridge includes a chamber for holding unused calibration fluid, a flow channel configured to receive calibration fluid from the chamber and to provide calibration fluid to an output, and a pinch valve configured to control the flow of the calibration fluid through the fluid channel. In this embodiment, the calibration fluid cartridge does not carry a mechanism controlling actuation of the pinch valve.

Another embodiment of the present disclosure relates to a calibration fluid cartridge for a diagnostic device. The calibration fluid cartridge includes a chamber for holding unused calibration fluid, a flow channel configured to receive calibration fluid from the chamber and to provide calibration fluid to an output, a junction for receiving gas in the flow channel, and a system of valves such that gas and calibration fluid can controllably flow to the output.

Another embodiment of the present disclosure relates to a disposable assay cartridge including a housing having at least a top end and a bottom end. The top end includes an inlet, including an interface for accepting a receptacle containing a sample fluid. The disposable assay cartridge further includes a sample fluid channel in fluid communication with the inlet for receiving sample fluid, the sample fluid channel being interrupted by a valve that controls a flow of sample fluid into an interior fluid channel that is in fluid communication with (i) a calibration fluid channel, (ii) an array comprising a plurality of electrochemical sensors, and (iii) a waste area downstream of the array comprising a plurality of electrochemical sensors for accepting spent fluids, including used calibration fluid. In this embodiment, the bottom end includes a second inlet for introducing calibration fluid or air into the calibration fluid channel and an outlet for communication with pressure or vacuum pump for aspiration of calibration fluid, air, or sample fluid.

Another embodiment of the present disclosure relates to a valve control mechanism for a diagnostic device configured to receive a removable assay cartridge. The valve control mechanism includes a cam plate configured to rotate, the cam plate having one or more concentric grooves comprising one or more raised portions, one or more valve actuators having one or more guides, the guides configured to align with the concentric grooves, maintaining contact with the grooves as the cam plate rotates. The valve actuators are configured to actuate one or more valves when the guides encounter the raised portion of the cam plate, and the valves are configured to control at least the flow of fluid in the removable assay cartridge.

BRIEF DESCRIPTION OF THE FIGURES

The disclosure will become more fully understood from the following detailed description, taken in conjunction with the accompanying figures, wherein like reference numerals refer to like elements, in which:

FIG. 16 is a back view of the assay cartridge of FIG. 15 with fluid filling the cartridge, according to an alternative embodiment.

FIG. 17 is a linear representation of the fluid flow path through the assay cartridge of FIG. 15.

FIG. 28 is a perspective semi-transparent view of a calibration cartridge, according to an exemplary embodiment.

FIG. 29 is a cross-sectional side view of the calibration cartridge of FIG. 28, including a fluid pack, according to an exemplary embodiment.

FIG. 30 is a close up cross-sectional view of a rod valve of the calibration cartridge of FIG. 28, including the rod valve in the open and closed position, according to an exemplary embodiment.

FIG. 35 is a perspective and semi-transparent view of a calibration cartridge, according to an alternative embodiment.

FIG. 36 is a cross-sectional view of the calibration cartridge of FIG. 35, including a fluid pack and a T connector, according to an alternative embodiment.

FIG. 39 is another perspective view of the calibration cartridge of FIG. 35, showing pinch valve actuators engaging the pinch valves of the calibration cartridge to regulate fluid and/or gas flow, according to an exemplary embodiment.

FIG. 40 is a cross-sectional view of the calibration cartridge of FIG. 39 including pinch valve actuators engaging the pinch valves of the calibration cartridge.

FIG. 41 is a close up cross-sectional view of a calibration cartridge pinch valve in the open and closed position, according to an exemplary embodiment.

DETAILED DESCRIPTION

Figure 1:
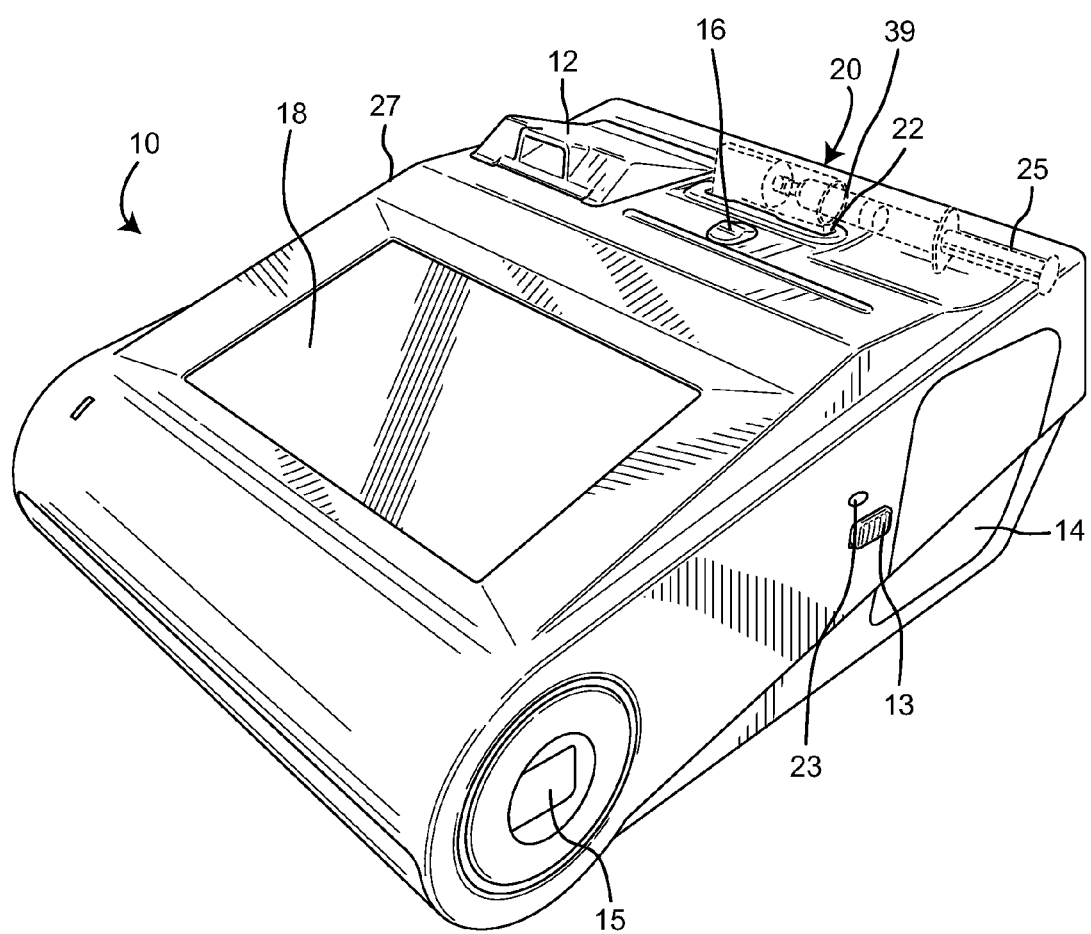
FIG. 1 is a perspective view of an in vitro medical diagnostic device and attached assay cartridge, according to an exemplary embodiment.

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

The present disclosure relates to an in vitro medical diagnostic device 10 that includes a removable and saleable solution reservoir, or calibration cartridge 30. The device also includes a removable assay cartridge 20. In an exemplary embodiment, the removable assay cartridge 20 includes a polymer body with channels 32 for fluid movement, a valving system for changing or sealing fluid paths, a receiving port 34 for receiving fluid samples 39, and a plurality of sensors 57. The diagnostic device 10 can interpret the inputs from the sensors 57, conduct diagnostics using the inputs from the sensors 57, and output information (e.g., via display, via printed report, etc.).

Figure 2:
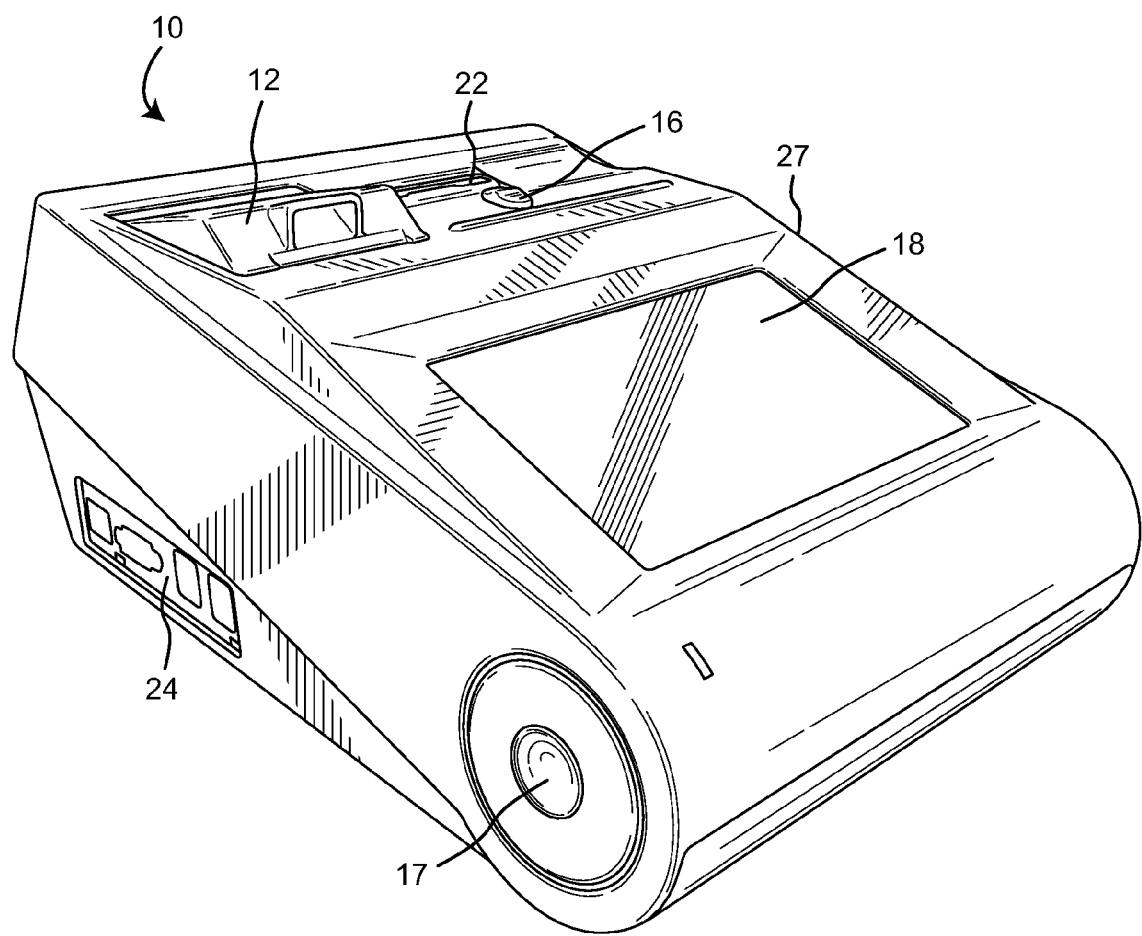
FIG. 2 is a perspective view of the in vitro medical diagnostic device of FIG. 1.
Figure 3:
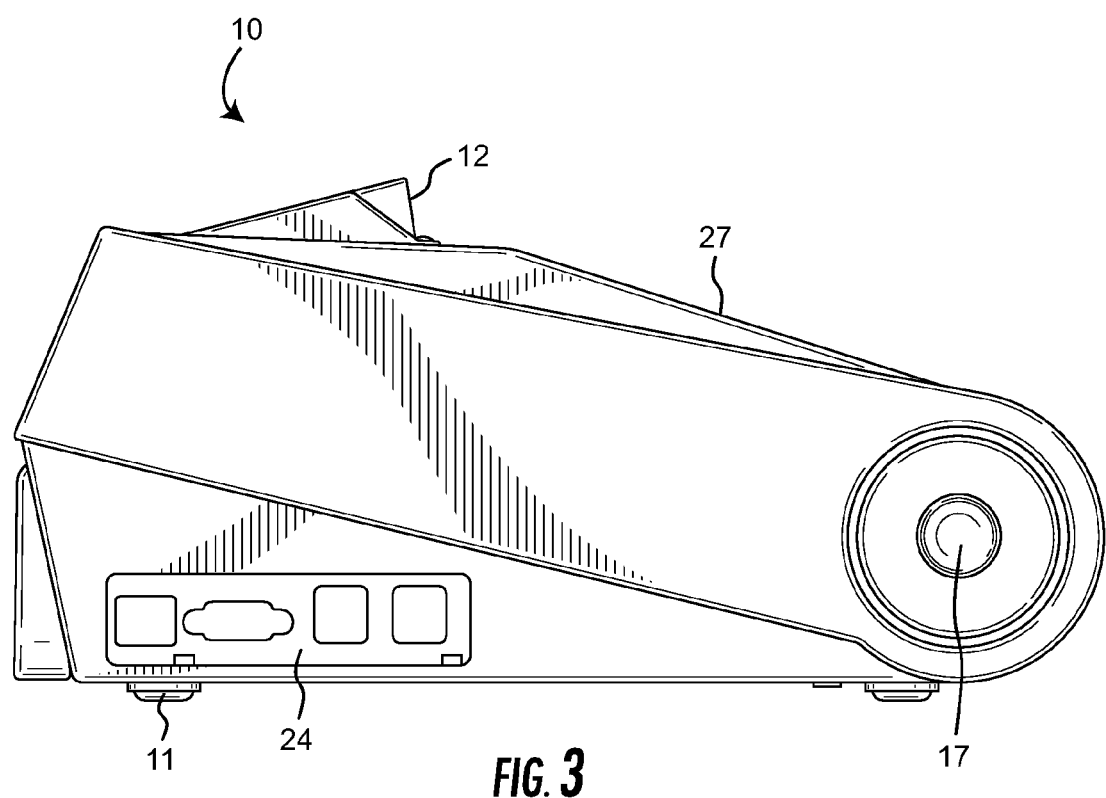
FIG. 3 is a side view of the in vitro medical diagnostic device of FIG. 1.
Figure 4:
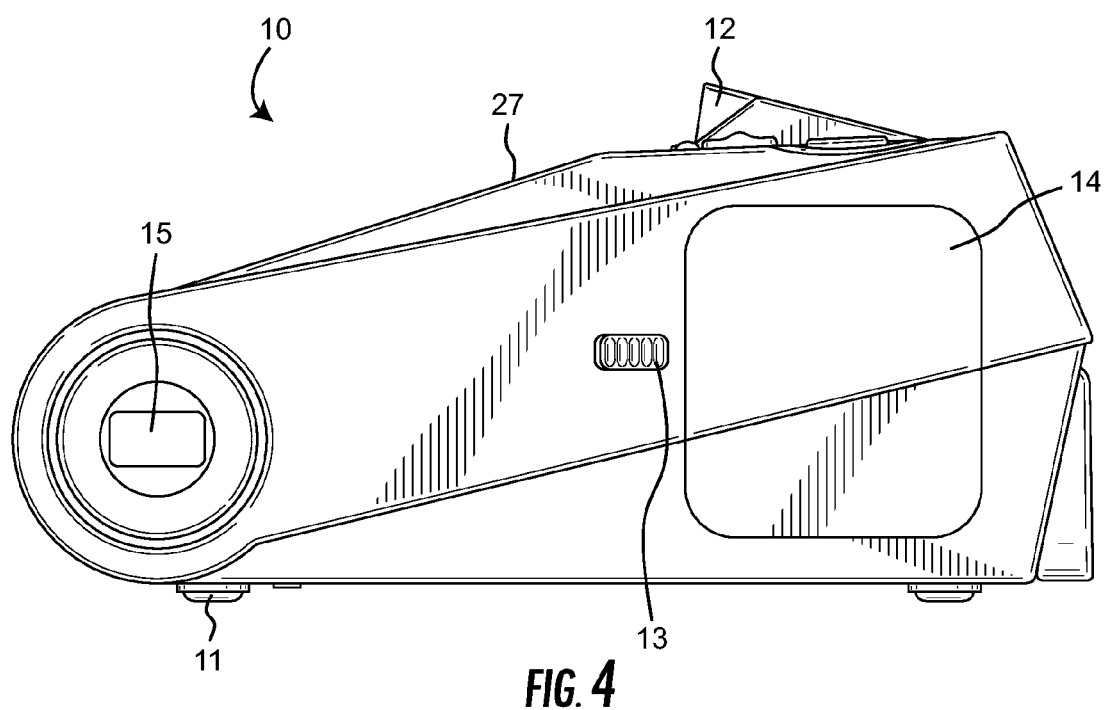
FIG. 4 is another side view of the in vitro medical diagnostic device of FIG. 1.
Figure 5:
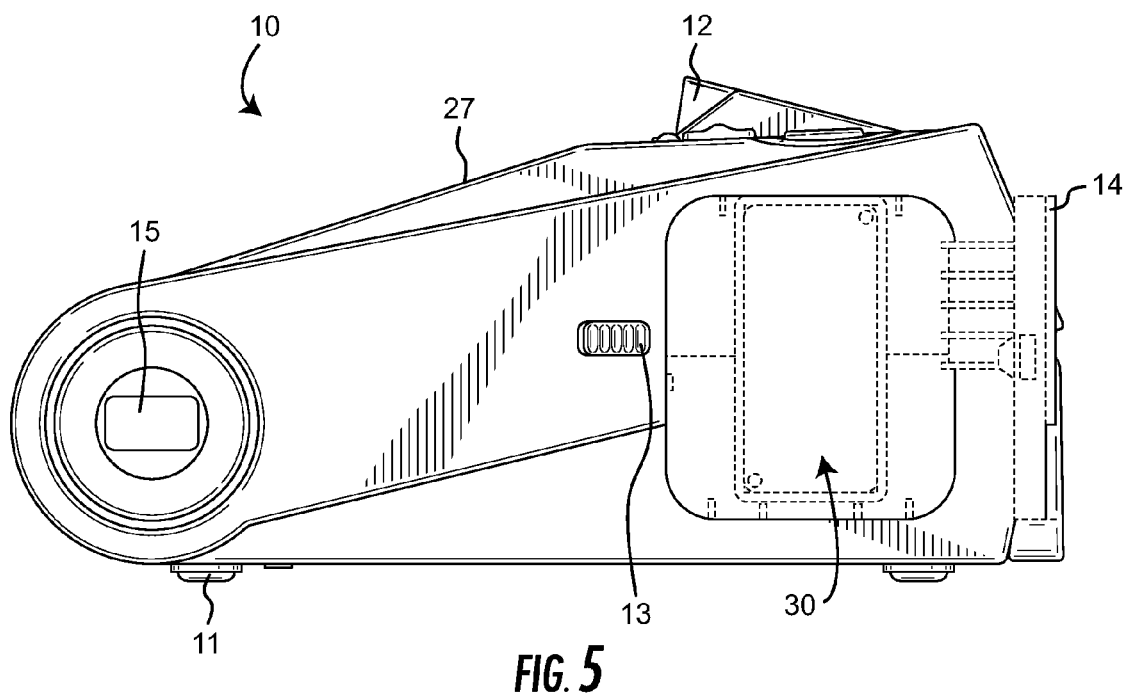
FIG. 5 is another side view of the in vitro medical diagnostic device of FIG. 1, this view illustrating an open door 14 and the placement of a calibration cartridge 30 within the medical diagnostic device, according to an exemplary embodiment.
Figure 6:
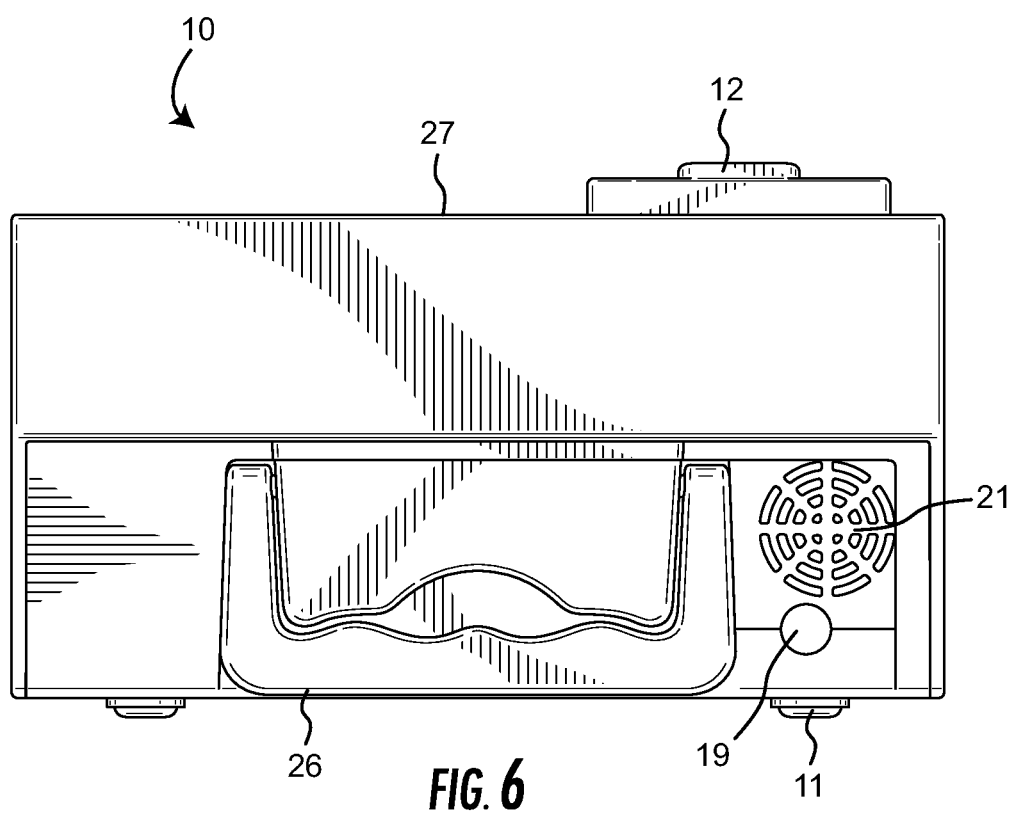
FIG. 6 is a back view of the in vitro medical diagnostic device of FIG. 1.

Referring to FIGS. 1-6, an in vitro medical diagnostic device of the present disclosure is shown, according to an exemplary embodiment. FIG. 1 is a perspective view of the in vitro medical diagnostic device 10 shown with the removable assay cartridge 20 fully inserted into the device 10. FIG. 2 is a perspective view of the in vitro medical diagnostic device 10. FIG. 3 is a side view of the in vitro medical diagnostic device 10. FIG. 4 is another side view of the in vitro medical diagnostic device 10. FIG. 5 is another side view of the in vitro medical diagnostic device 10 of FIG. 1, this view illustrating an open door 14 and the placement of a calibration cartridge 30 within the medical diagnostic device, according to an exemplary embodiment. FIG. 6 is a back view of the in vitro medical diagnostic device 10.

The in vitro medical diagnostic device 10 has a housing 27 that provides a shell for the device 10. The housing 27 may be plastic or any other material suitable for the application. The in vitro diagnostic device 10 is configured to receive an assay cartridge 20 (shown further in FIGS. 7-9). The assay cartridge 20 is inserted into a testing slot 22. In the illustrated embodiment of FIG. 1, a syringe 25 holding a fluid sample 39 (i.e. biological sample, drug sample, etc.) is used to dispense the fluid sample 39 into the cartridge 20. The device 10 is configured to test the fluid sample 39, and to report the results to a user via an output. In the illustrated embodiment of FIG. 1, the device 10 is shown to include a display screen 18 for providing the output. However, in this or other embodiments, the results may also or alternatively be reported to the user by other outputs, including audio outputs, data communication outputs, or a printout.

In exemplary embodiments, the assay cartridge 20 may be removed from the device 10 once the fluid sample 39 is tested. The device 10 may include an eject button 16, which the user may press to eject the cartridge 20 from the testing slot 22 once the testing has completed. The device 10 may also be configured to eject the cartridge 20 automatically when the testing cycle has completed. In exemplary embodiments, the assay cartridge 20 is disposable (i.e. the cartridge 20 can be removed and replaced). The assay cartridge 20 may be single-use (i.e. used once and replaced with another cartridge 20) in some exemplary embodiments. In other exemplary embodiments, the cartridge 20 may be re-cycled and used to test more than one fluid sample 39. The diagnostic device 10 is intended to be portable, having a handle 26 for carrying the portable device 10 and being sized to fit on a tabletop.

In exemplary embodiments, the diagnostic results are reported on a display screen 18. Processing electronics of the device 10 can cause the display 18 to display information relevant to the particular application. The display screen 18 may be a one-way screen configured to display output to a user, or may be a touch screen configured to receive and respond to user touch input. In exemplary embodiments, the diagnostic device also includes a printer slot 12 configured to receive a paper output by a printer housed within the device 10.

Figure 47:
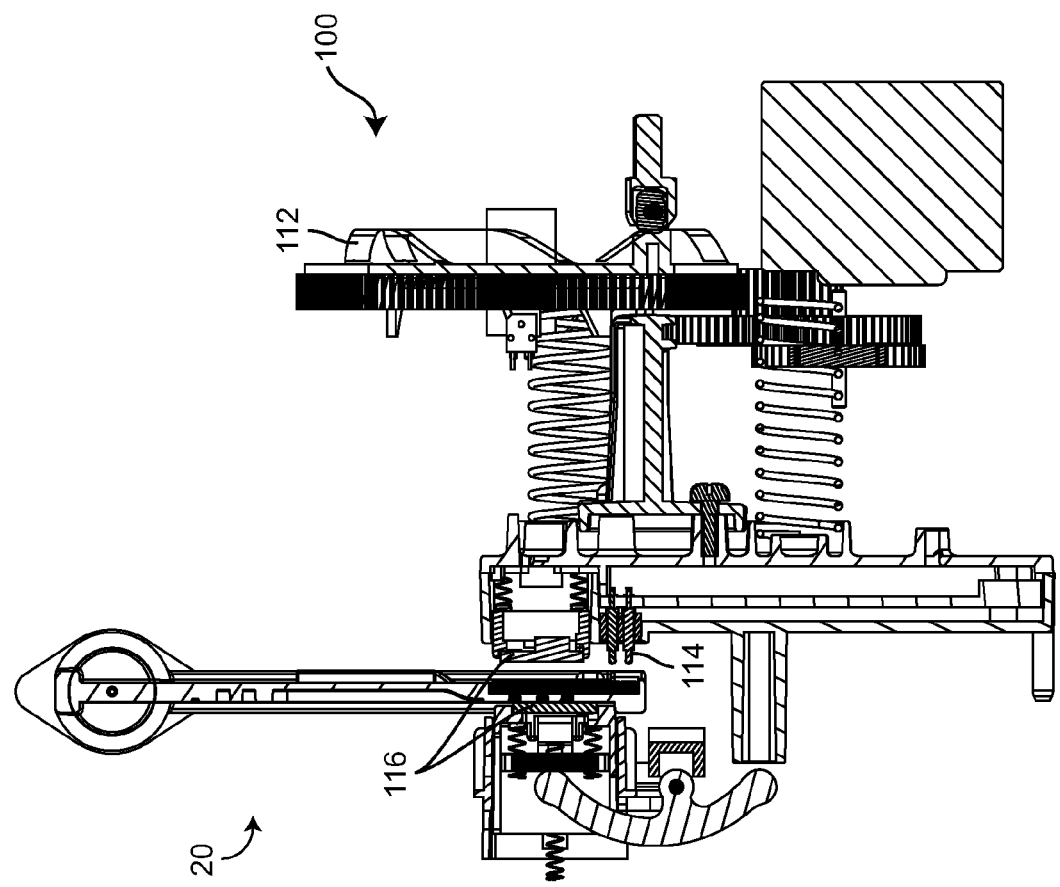
FIG. 47 is a side view of a motor assembly for controlling pinch valve actuators for a diagnostic device, according to an exemplary embodiment.

The diagnostic device 10 may also include one or more heating elements 116 (e.g. as shown in FIG. 47). In exemplary embodiments, the heating elements 116 are one or more heating plates located within the testing slot 22 of the device 10. In the illustrated embodiment of FIGS. 1-6, two heating elements 116 are configured such that there is a heating element 116 located on each side of the assay cartridge 20 when the assay cartridge 20 is inserted into the device 10. The heating elements 116 are caused to control the heat of the fluid (e.g. fluid sample 39, calibration fluid, etc.) within a testing portion 42 of the assay cartridge 20, causing the fluid to maintain a substantially constant temperature. In exemplary embodiments, the heating elements 116 are controlled to hold the fluid at a substantially constant temperature of approximately 37 degrees Celsius (approximately 98.6 degrees Fahrenheit). The testing portion 42 may include a plurality of apertures (i.e. fluid reservoirs) positioned along one or more of the planar heating elements 116 (i.e. heating plates). The apertures are configured to hold the fluid within the testing portion 42, so that the heating elements 116 can control the temperature of the fluid.

According to the illustrated embodiment of FIG. 1-6, the in vitro medical diagnostic device 10 also includes a calibration cartridge door 14. The calibration cartridge door 14 is shown to open away from the device 10. The calibration cartridge door 14 and the opening behind the door 14 are sized to receive a disposable calibration cartridge 30 (shown in further detail in FIGS. 28-43). The calibration cartridge door 14 is opened by a door latch 13 in the illustrated embodiments, but may be opened by other mechanisms in other exemplary embodiments. The door latch 13 is located adjacent to the door 14. Behind the calibration cartridge door 14 is a calibration cartridge port configured to receive the calibration cartridge 30.

In exemplary embodiments, the device 10 includes a calibration door lock 23 located next to the door 14. The calibration door lock 23 has a locked position and an unlocked position, and may be toggled between the two positions by a calibration door key. In some exemplary embodiments, the calibration door key is found in a calibration cartridge cover (described in further detail in the specification below). In other embodiments, the calibration door key may be found in other locations on the device 10, or may be a separate piece from the device 10 or the calibration cartridge 30. The calibration door key may be removed from the cover or other location and is configured to lock or unlock the calibration door lock 23. When the door lock 23 is in the locked position, the calibration cartridge door 14 is locked and will not open. The calibration door lock 23 is configured to prevent tampering with the calibration cartridge 30. In yet other embodiments, the door lock 23 is engaged by default when the door is closed and must be opened via a pass code entered via user interface keys (e.g. soft keys on a display, hard keys of a keypad, etc.).

The in vitro medical diagnostic device 10 may include one or more ports 24 (shown in FIG. 3), in exemplary embodiments. These ports 24 are configured to receive cables or other connection mechanisms. The ports 24 may be used to connect the device 10 to other pieces of equipment (e.g. via a communication network), or may be used to upload or download information to the device 10. The device 10 may also be configured to exchange data wirelessly, including through Wi-Fi, another wireless internet connection, or by any other wireless information exchange. The device 10 also includes a power input 19, which may receive a power supply connection that charges or provides power to the device 10. The device 10 also includes a speaker 21, which may be used to transmit a noise or audible response to the user. The device 10 may also include a handle 26, which can be used to carry the portable device 10. The handle 26 rotates between two positions, depending on whether it is in use. In the illustrated embodiment of FIG. 6, the handle 26 is not in use, so it is rotated down and against the back surface of the device 10, out of the way of the user. In exemplary embodiments, the device 10 may also include support legs 11 configured to allow the device 10 to rest on a table top or other surface.

The device 10 may also include a light source (e.g. LED) located to illuminate the assay cartridge 20. The light source may be configured to illuminate the assay cartridge 20 to indicate testing status, or for any other purpose suitable for the particular application. The light source may be a fluorescent light, or may be any other type of light as necessary or desirable for the particular application.

The device 10 also includes a bar code scanner 15 that is built into the side of the device 10, in exemplary embodiments. The bar code scanner 15 is configured to scan bar codes on test assay cartridges 20, calibration fluid packs 54, liquid quality control solutions, or any other items having scannable bar codes and for use with the device 10. The bar code scanner 15 may also be used to scan a bar code tag representing patient or operator identification. In exemplary embodiments, the scanner 15 emits a beam that covers the bar code. If the bar code is scanned successfully, the device 10 will beep and the beam will turn off automatically. If the bar code is not scanned successfully, the device 10 will prompt the user through the display screen 18, by emitting a noise, or by some other output. In an exemplary embodiment, the bar code scanner 15 is a one-dimensional bar code scanner. In other embodiments, the bar code scanner 15 is a two-dimensional scanner.

Figure 7:
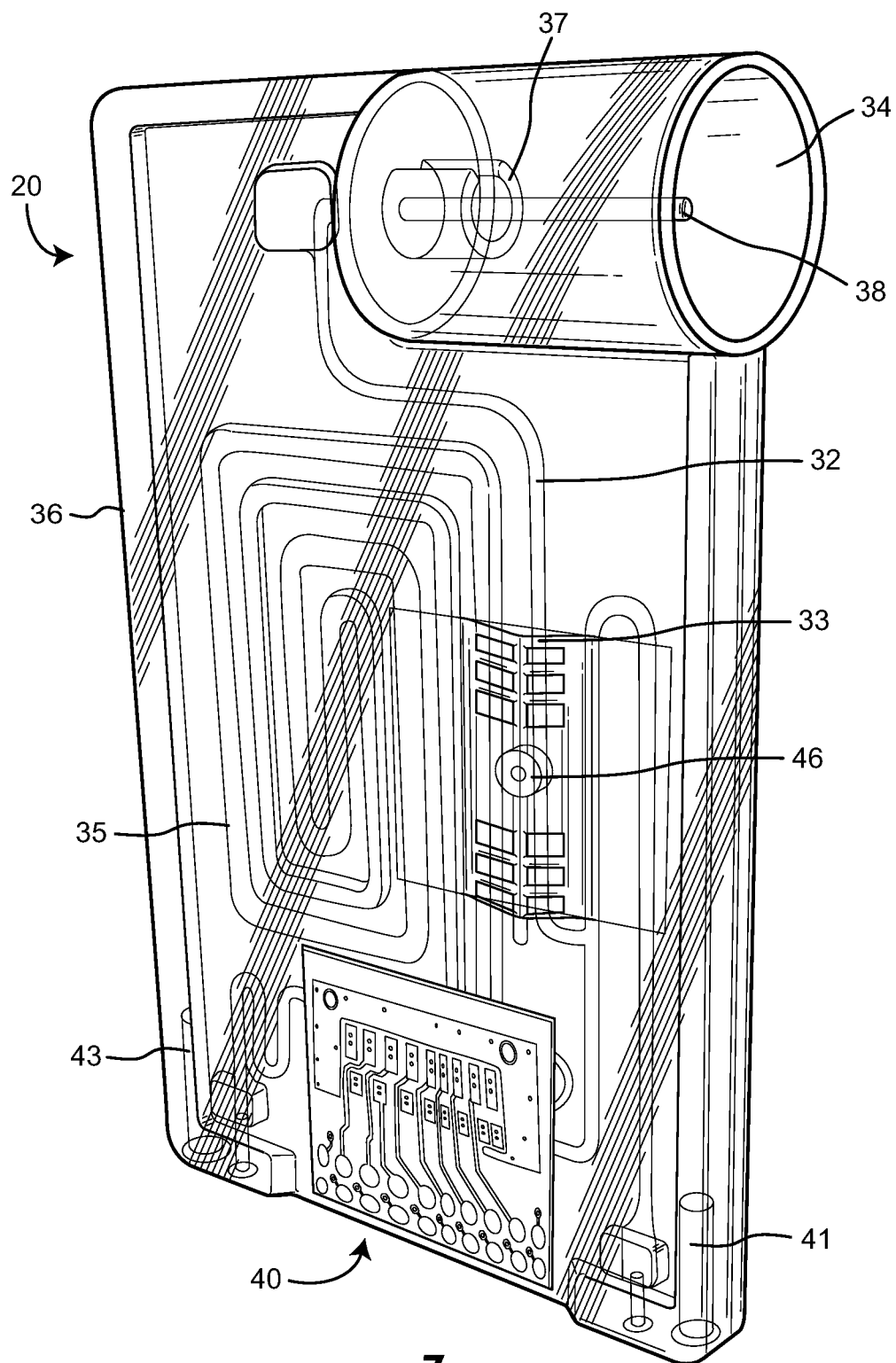
FIG. 7 is a perspective view of an assay cartridge for insertion into the medical diagnostic device, according to an exemplary embodiment.
Figure 8:
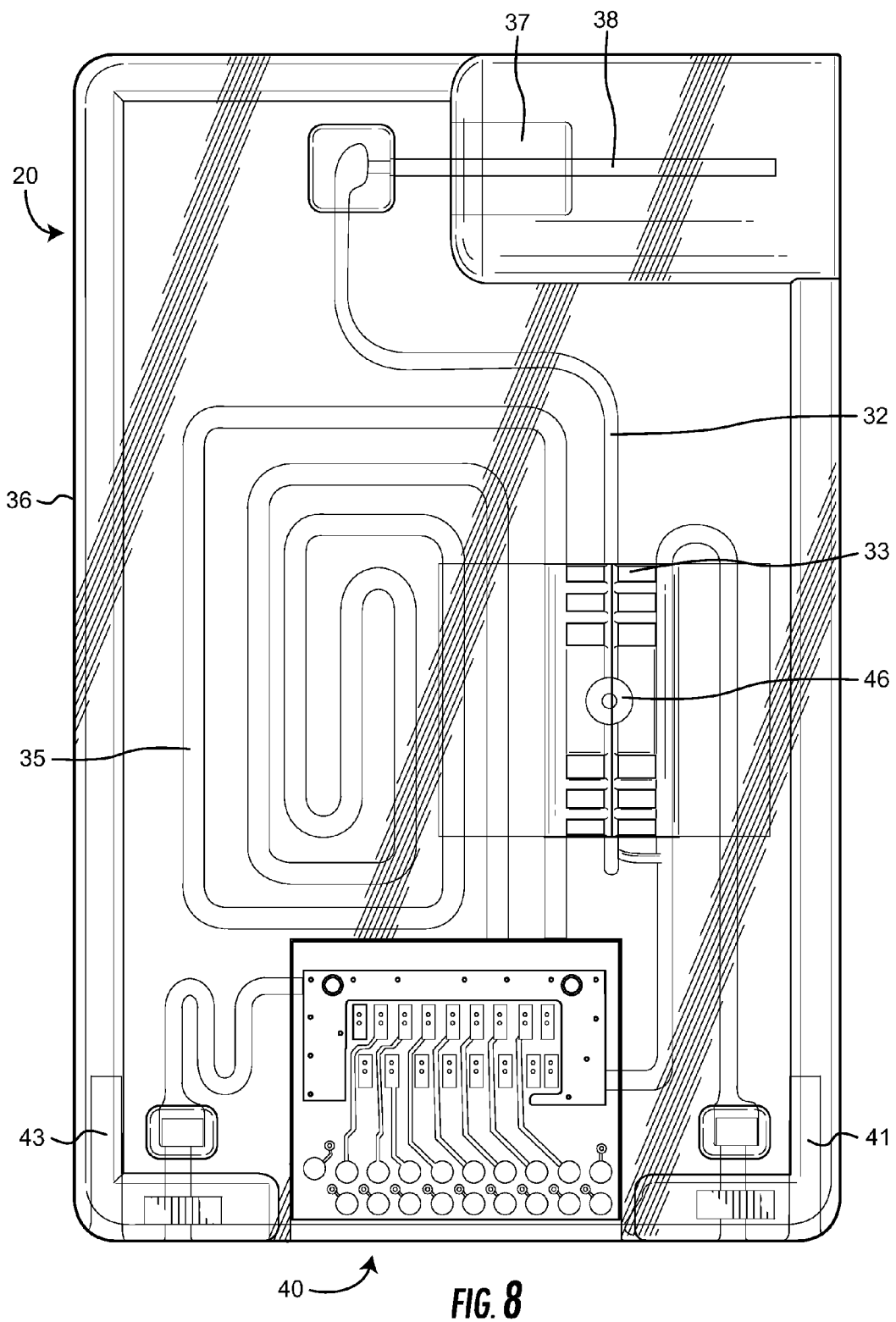
FIG. 8 is a front view of the assay cartridge of FIG. 7.
Figure 9:
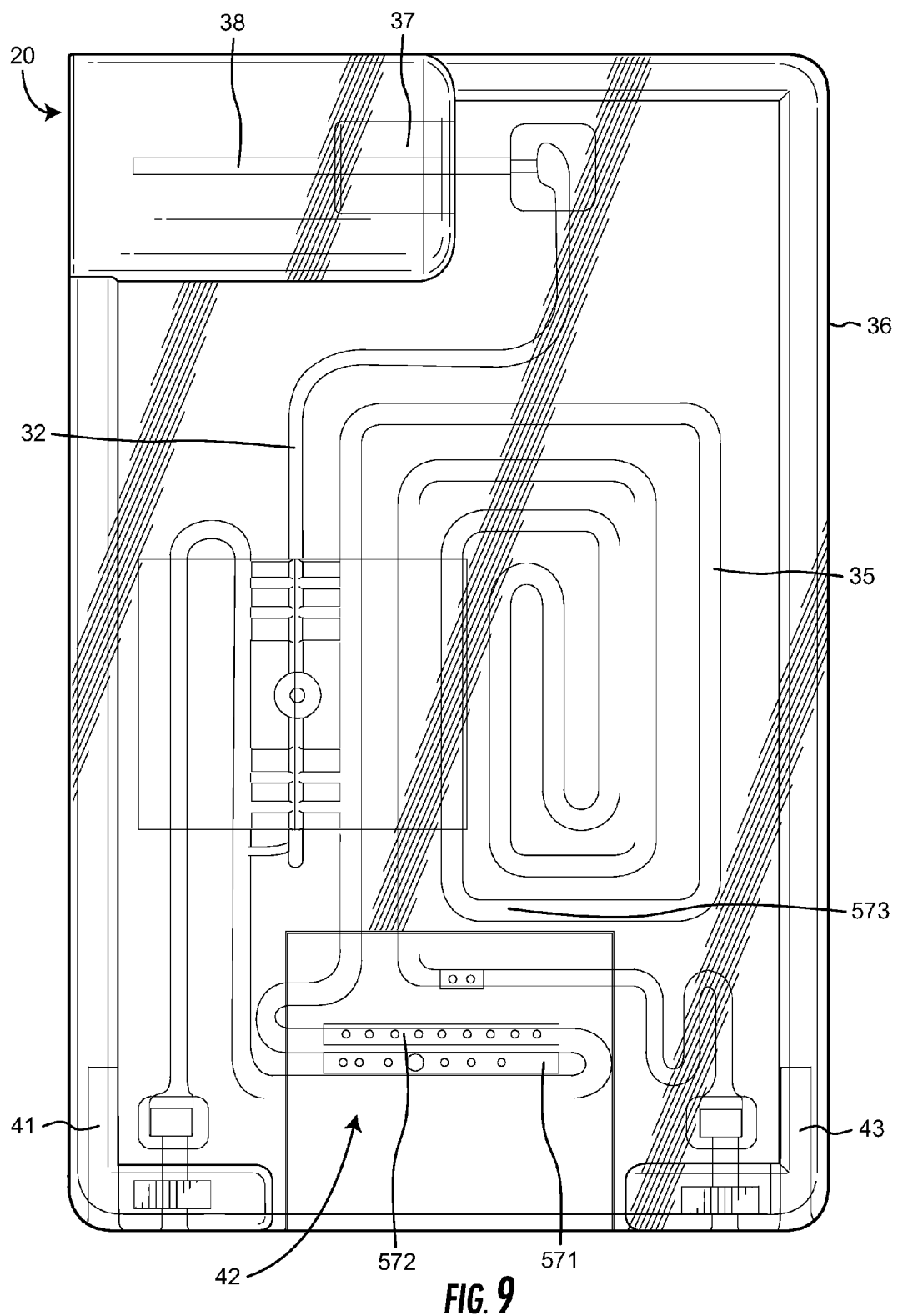
FIG. 9 is a back view of the assay cartridge of FIG. 7.

Referring now to FIGS. 7-9, the assay cartridge 20 is shown, according to an exemplary embodiment. The assay cartridge 20 includes a cartridge body 36. In exemplary embodiments, the cartridge body 36 is at least partially transparent. The cartridge body 36 may be made from a molded plastic, or from another material, or set of material. The cartridge body 36 provides protection for the cartridge 20. In the illustrated embodiment of FIGS. 7-9, at least one portion of the cartridge body 36 is covered with a thin film for sealing a channel or other components within the cartridge 20. The thin film may reduce the total thermal mass to be heated by the device 10. The cartridge has a top end (as shown in FIG. 7) for receiving a syringe 25 having a biological sample, and a bottom end that is inserted into the diagnostic device 10. The bottom end of the cartridge 20 is configured to insert into the testing slot 22 of the diagnostic device 10.

The assay cartridge 20 includes a stop member 33, in exemplary embodiments. The stop member 33 is located on the outside of the cartridge body 36 and is raised above the surrounding surface of the cartridge body 36. The stop member 33 is configured to lock the assay cartridge 20 into the device 10. One or more position detectors within the device 10 may be utilized to determine the position of the assay cartridge 20 (i.e. whether the cartridge is fully seated). A main board (shown in FIG. 44) having a processor may be configured to track a position for the assay cartridge 20 using information from at least one position detector. Once the assay cartridge 20 has been fully inserted into the testing slot 22, a locking rod 120 (shown in FIG. 50) may actuate, protruding into a space adjacent (e.g. just above) to the stop member 33, and between the stop member 33 and the opening of the testing slot 22. Once the locking rod 120 is in this position, the cartridge 20 cannot be removed from the device 10 because the protruding surface of the stop member 33 is unable to clear the actuated locking rod 120. In exemplary embodiments, the user may press the eject button 16 to retract the locking rod 120, allowing the assay cartridge 20 to be removed from the testing slot 22. In other exemplary embodiments, a motor assembly 100 (shown in FIGS. 46-52) may automatically retract the locking rod 120 when the testing cycle has completed, allowing the assay cartridge 20 to be removed from the testing slot 22 without the user needing to manually activate an eject button 16. In other exemplary embodiments, the assay cartridge 20 is pushed up and out of the testing slot 22 by an automated mechanism when the eject button 16 has been pressed, or when the motor assembly 100 has otherwise retracted the locking rod 120.

Figure 10:
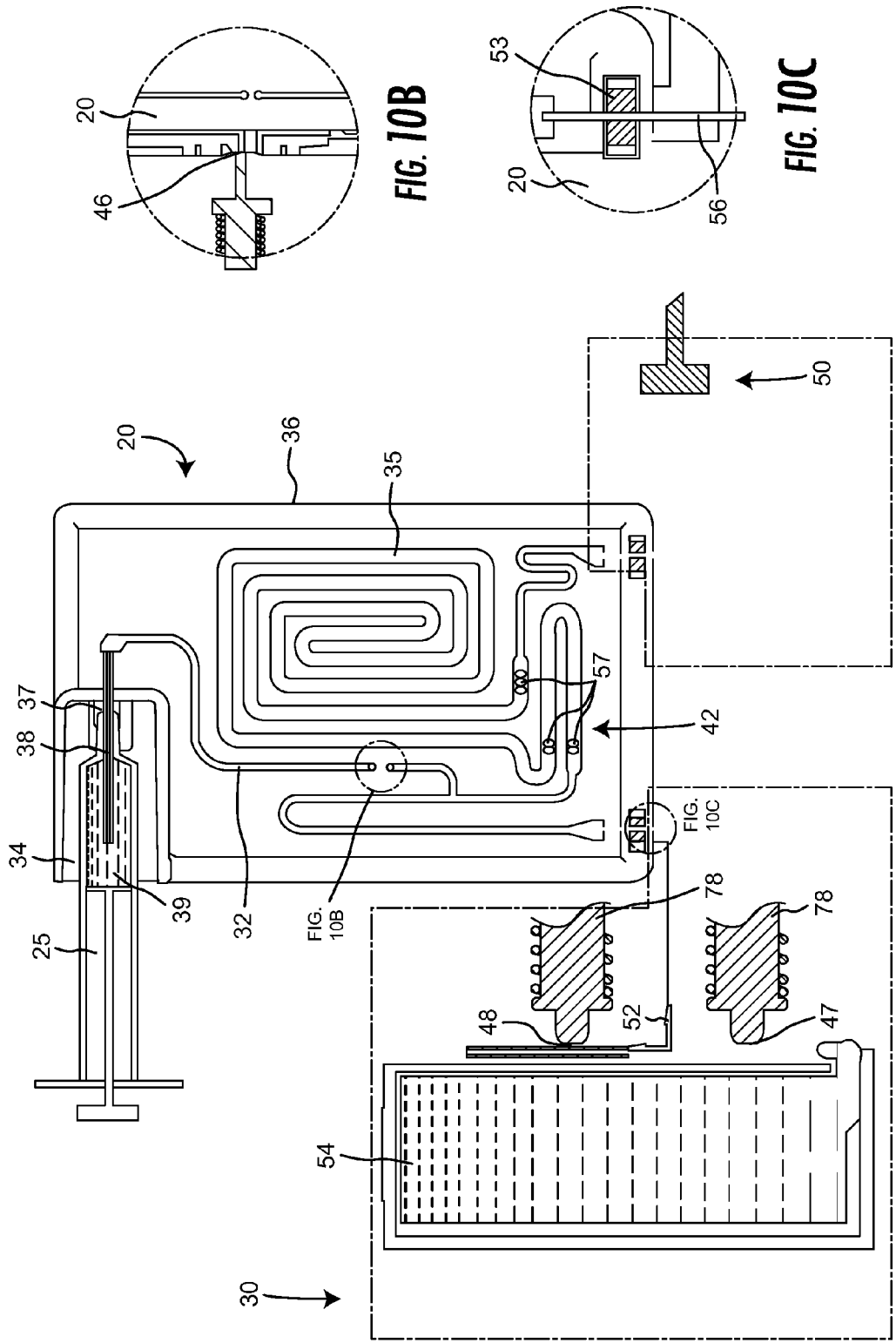
FIG. 10A is a schematic view of a system provided by the diagnostic device, including a calibration cartridge, an assay cartridge, a fluid path, and a pump, according to an exemplary embodiment.
FIG. 10B is a close up view of a point on the fluid path of the assay cartridge where the calibration fluid channel and the fluid sample channel meet, according to an exemplary embodiment.
FIG. 10C is a close up view of the fluid path connection between the assay cartridge and the calibration cartridge, according to an exemplary embodiment.

The bottom end of the assay cartridge 20 also includes positioning slots 41 and 43 on each side of the cartridge 20. The positioning slots 41 and 43 are configured to engage positioning rods. The positioning slots 41 and 43 are intended to protect needles 56 (illustrated in FIG. 10) that project into the cartridge 20 to transmit fluid or air. The positioning slots 41 and 43, guide the cartridge 20 into its testing position, protecting the needles 56 from bending or damage when the cartridge 20 is dislocated horizontally.

In exemplary embodiments, the assay cartridge 20 includes an inlet 34 located on the top end of the cartridge 20. The inlet 34 houses an interface 38 (e.g. needle) for connecting to a receptacle (e.g. syringe, capillary tube, etc.) containing a fluid sample 39. The assay cartridge 20 also includes a C-shaped structure 37 that is located within the inlet 34. In exemplary embodiments, the C-shaped structure 37 is a sleeve for the syringe 25, holding the tip of the syringe 25 within the inlet 34. The receptacle introduces the fluid sample 39 to the assay cartridge 20 for testing. The fluid sample 39 is received through the interface 38, and enters a fluid channel 32 within the cartridge 20. In some exemplary embodiments, the length of the interface 38 from the tip of the interface 38 to the end of the C-shaped structure 37 is approximately 21.6 mm, but may be another length in other embodiments.

In exemplary embodiments, the fluid channel 32 is fluidly connected to the testing portion 42 located on the bottom of the cartridge 20. The fluid channel 32 is configured to route the sample 39 to the testing portion 42. The testing portion 42 includes an array comprising a plurality of electrochemical sensors 40 for testing the fluid sample 39. The electrochemical sensors 40 are configured to communicate with hardware (illustrated in FIG. 44) within the diagnostic device 10 to provide diagnostic information to the user. The testing portion 42 is fluidly connected to a waste area 35 downstream of the fluid channel 32. In exemplary embodiments, the waste area 35 holds spent fluids, such as a calibration fluid.

The fluid channel 32 may have a larger or smaller diameter at certain points throughout the flow path (i.e. fluid channel 32, waste area 35, etc.). For instance, the fluid channel 32 may ramp up prior to or as it enters the testing portion 42, providing a smaller flow area or diameter. The fluid channel may then open up in the testing portion 42, creating larger area or diameter channels over the sensors 40 for holding and testing the fluid sample 39. The fluid channel 32 may also contain these "ramped" areas (i.e. areas where the fluid channel changes diameter) in portions of the waste area 35. These ramped areas within the waste area may be configured to keep a larger used volume of the calibration fluid within the waste area, preventing the fluid sample 39 from being contaminated. The ramped areas may also be present to slow down fluid flow within an area of the fluid channel 32.

FIG. 7 is a perspective view of an assay cartridge for insertion into the medical diagnostic device, according to an exemplary embodiment. FIG. 8 is a front view of the assay cartridge of FIG. 7. FIG. 9 is a back view of the assay cartridge of FIG. 7.

Referring now to FIGS. 10A-C, a schematic view of a system provided by the diagnostic device 10 is shown according to an exemplary embodiment, including the assay cartridge 20 as inserted into the diagnostic device 10, a fluid path, and a pump. According to the illustrated embodiment of FIG. 10A, the assay cartridge 20 is fluidly connected to the calibration cartridge 30 on a first side, and connected to a vacuum pump 50 on a second side. In exemplary embodiments, the calibration cartridge 30 is configured to introduce gas or fluid into the assay cartridge 20 through a T connector 52 (shown in more detail in FIGS. 28-43). The T connector (i.e. air and gas junction) 52 may connect to the assay cartridge 20 by a needle 56 or another connection mechanism.

One or more pinch valves 46-48 control the sequence of gas or fluid flows from the calibration cartridge 30 to the assay cartridge 20. In exemplary embodiments, two pinch valves 47 and 48 regulate the introduction of calibration fluid and air into the assay cartridge 20, while one pinch valve 46 regulates the introduction of the fluid sample 39 into the testing portion 42. In other embodiments, a different system of pinch valves may regulate the flow of fluid in the cartridge 20.

FIG. 10A shows a fluid flow path through the assay cartridge 20. In exemplary embodiments, the inlet 34 receives a syringe 25, or other receptacle such as a capillary tube, filled with the fluid sample 39 (i.e. biological sample). The interface 38 of the inlet 34 enters the tip of the syringe 25 and protrudes into the fluid sample 39. The interface 38 is fluidly connected to the fluid sample 39 within the syringe 25, and fluidly connects the fluid sample 39 to the fluid channel 32.

FIG. 10B shows a linear pathway for the fluid sample 39 to flow through the fluid channel 32 and into the testing portion 42. The fluid flow is unidirectional, in exemplary embodiments. Fluid may flow from the syringe 25 (or other receptacle) to the pinch valve 46 in the assay cartridge 20. From the pinch valve 46, the fluid flows in a single direction. The pinch valve 46 is configured to open and close, controlling (e.g. allowing or preventing) the introduction of the fluid sample 39 into the testing portion 42. The fluid travels through the fluid channel 32, through the testing portion 42, and if necessary, into the waste area 35.

Once the fluid channel 32 is filled, the pressure in the fluid channel 32 dissipates and fluid is prevented from flowing out of the disposable assay cartridge 20. The volume of the fluid channel 32 may be known and accordingly a complementary volume of fluid allowed into the channel 32 may be controlled to prevent overflow of the cartridge 20. In exemplary embodiments, the fluid (e.g. fluid sample 39, calibration fluid, etc.) used during a testing procedure is completely contained within the assay cartridge 20. As can be seen in the illustration of FIG. 10A, there is no fluid communication from the assay cartridge 20 to any surface of the diagnostic device 10 and no fluid communication from the calibration cartridge 30 to any surface of the diagnostic device 10. The assay cartridge 20 is removable and disposable. Accordingly, there is no fluidic circuitry inside the diagnostic device 10, which may reduce the potential risks and cleaning requirements associated with fluidic circuitry. The self-contained assay cartridge 20 is intended to prevent repairs or maintenance due to fluid leaking and corroding sensitive electronics in the device 10, potentially reducing the maintenance costs associated with the device 10. The fluid sample 39 (or other fluid) travels through the cartridge 20 uni-directionally, is completely contained within the cartridge 20 (during and even after testing), and does not enter any other part of the device 10.

In exemplary embodiments, the vacuum pump 50 is also fluidly connected to the fluid channel 32. The vacuum pump 50 may be powered on and off and controllably operated by the diagnostic device 10. When the vacuum pump 50 is powered on, it may create a controlled negative pressure in the assay cartridge 20, driving the fluid sample 39 to flow from the syringe 25 and into the fluid channel 32. A pinch valve 46 may be used to open or close the fluid channel 32, allowing the fluid sample 39 to travel into the testing portion 42. Pinch valves 48 and 47 are also used to control the introduction of atmospheric air and calibration fluid, respectively, from the calibration cartridge 30 to the assay cartridge 20. The pinch valves 46-48 may be controlled by control hardware (illustrated in FIG. 44) within the device 10, and opened or closed in sequence to complete the testing cycle.

By controllably powering the vacuum pump 50 on or off, and opening or closing the pinch valves 46-48, the calibration fluid, atmospheric air (or another gas), and fluid sample 39 may enter the assay cartridge 20 in a designated sequence. In exemplary embodiments, the calibration fluid enters the assay cartridge 20 first. The pinch valve 47 is controllably opened, and the pinch valves 46 and 48 are controllably closed. Calibration fluid is then pumped from the calibration cartridge 30 to the assay cartridge 20, and into the testing portion 42. The calibration fluid is held in the testing portion 42 for a predetermined amount of time, heated to a predetermined temperature, and used to calibrate the device 10. Once the device 10 has been calibrated, the pinch valve 48 is controllably opened and the pinch valves 46 and 47 are controllably closed. Air is then pumped from the calibration cartridge 30 into the testing portion 42. The air pushes the calibration fluid into the waste area 35, clearing the testing portion 42. Once the calibration fluid has been cleared from the testing portion 42, the pinch valve 46 is controllably opened, and the pinch valves 47 and 48 are controllably closed. The fluid sample 39 is then pumped into the testing portion 42, where the sample 39 is heated and tested. Once the fluid sample 39 has been tested by the device 10, the testing cycle is complete and the assay cartridge 20 may be ejected.

In some exemplary embodiments, the pinch valves 46-48 may be integrated pinch valves, having a thin film that is elastically biased out and can be closed by applying pressure in toward the cartridge 20 or 30. In these embodiments, the pinch valves 46-48 include flexible film areas 76 (shown in FIG. 25). The pinch valves 46-48 may be constructed at least in part with polyethylene terephthalate. A pinch valve actuator 78 (e.g. movable lever) may be applied to the pinch valves 46-48 to open or close the pinch valves 46-48. The pinch valve actuator 78 may open or close the valves 46-48 by applying or removing pressure. The pinch valves 46-48 may close under pressure and open in the absence of pressure. Once the pinch valve 46 is open, the fluid sample 39 can travel from the syringe 25 or other receptacle, through the fluid channel 32, and to the testing portion 42.

Referring now to FIG. 10C, the connection (i.e. gas inlet or outlet) between the assay cartridge 20 and the calibration cartridge 30 is represented. In exemplary embodiments, the connection between the assay cartridge 20 and the calibration cartridge 30 includes a rubber seal 53, which forms a fluid seal at the needle 56. In these embodiments, the rubber seal 53 is attached to the T connector 52, and is configured to ensure a sealed connection for the fluid flow path between the assay cartridge 20 and the calibration cartridge 30. In exemplary embodiments, the rubber seal 53 is pierced to establish fluid communication between the calibration fluid channel 88 and the assay cartridge 20. The rubber seal 53 may be made from a septum comprising silicone, or any other material suitable for the application.

The fluid connection between the assay cartridge 20 and the vacuum pump 50 is similar to the connection shown in FIG. 10C. The connection between the assay cartridge 20 and the vacuum pump 50 includes a rubber seal 53 forming a fluid seal at the needle 56. The rubber seal 53 is attached to the vacuum pump 50 (i.e. forming a pumping system), and is configured to provide a fluid flow path between the assay cartridge 20 and the vacuum pump 50. The fluid flow path may be fluidly sealed. In exemplary embodiments, the assay cartridge 20 is also tapered at both connections in order to receive the needles 56, and is configured to establish a fluid seal. The rubber seal 53 may be made from a septum comprising silicone, or any other material suitable for the application.

Figure 11:
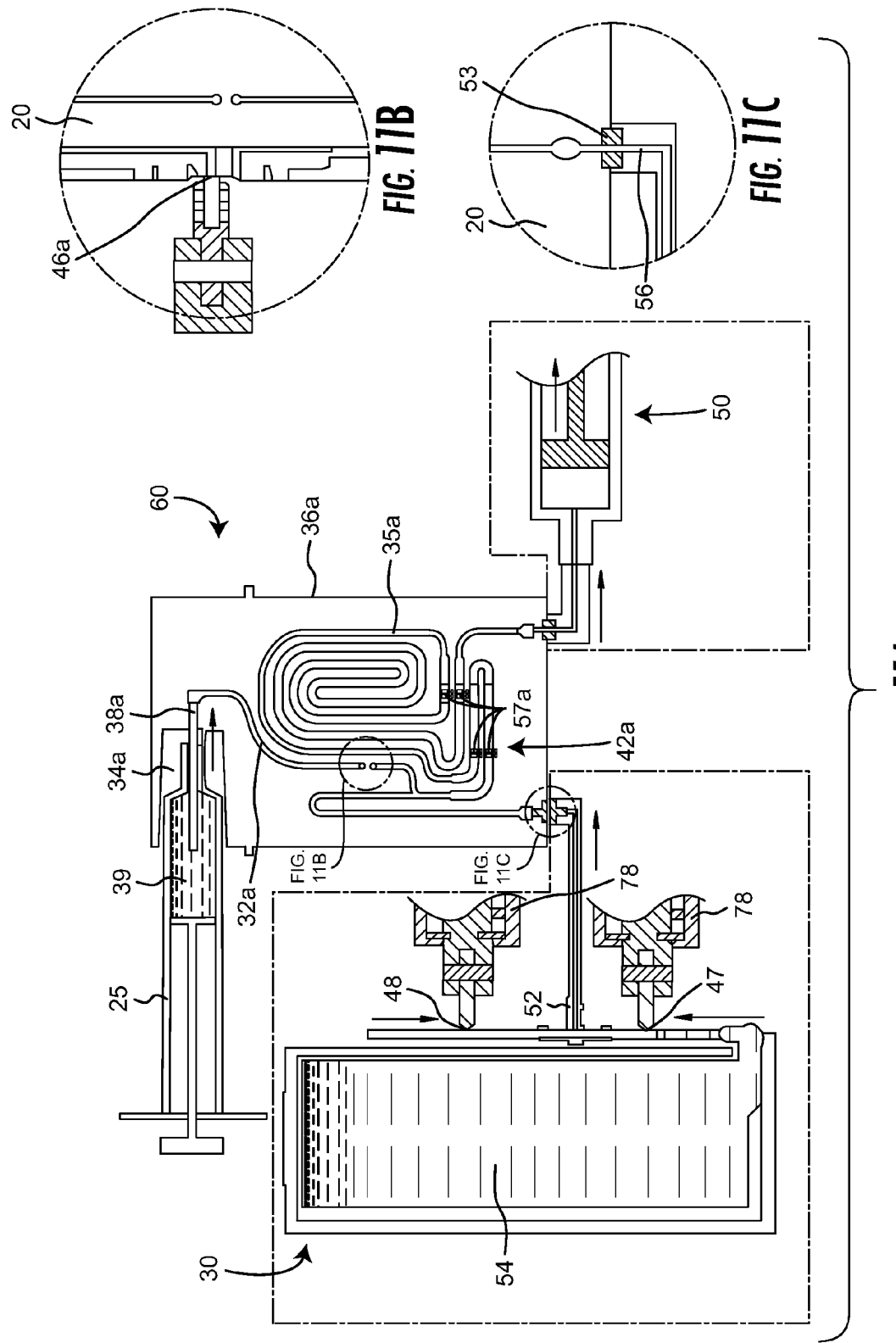
FIG. 11A is a schematic view of a calibration cartridge connected to an assay cartridge to form a fluid path for the flow of fluid actuated by a pump, according to an alternative embodiment.
FIG. 11B is a close up view of the point on the fluid path of the assay cartridge where the calibration fluid channel and the fluid sample channel meet, according to an alternative embodiment.
FIG. 11C is a close up view of the fluid path connection between the assay cartridge and the calibration cartridge, according to an alternative embodiment.

Referring briefly to FIGS. 11A-C, a schematic representation of a calibration cartridge 30 connected to an alternative assay cartridge 60 is shown, according to an alternative embodiment. The connection forms a fluid path for the fluid flow actuated by the pump 50. The alternative assay cartridge 60 is shown more particularly in FIGS. 15-17, and described later within this specification.

Figure 12:
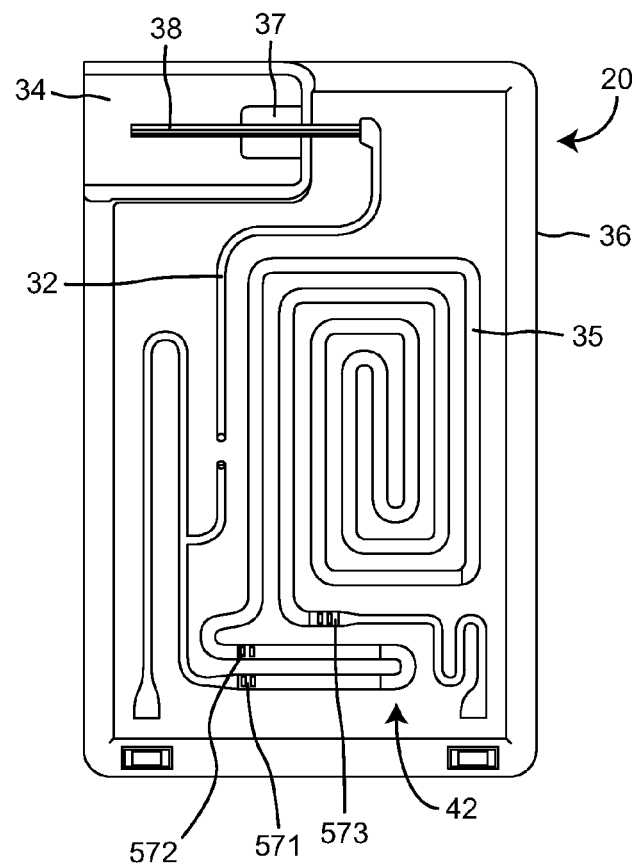
FIG. 12 is a simplified back view of the assay cartridge of FIG. 7.

Referring now to FIG. 12, a simplified back view of the assay cartridge 20 is shown, according to an exemplary embodiment. The assay cartridge 20 is configured to receive the fluid sample 39 through the interface 38. The fluid sample 39 is routed through the fluid channel 32, and then to the testing portion 42. The testing portion 42 includes a plurality of sensors 57, including electronic sensors 571 and 572. In the illustrated embodiment of FIG. 12, the electronic sensors 571 and 572 are configured to control the volume of fluid introduced into the assay cartridge 20. In exemplary embodiments, the assay cartridge 20 includes an overflow prevention sensor 573 positioned within the waste area 35. The overflow prevention sensor 573 is configured to send one or more signals to processing electronics when fluid reaches the overflow prevention sensor 573. The processing electronics are configured to stop the flow of fluid into the assay cartridge 20 one or more signals are received from the sensor 573.

Figure 14:
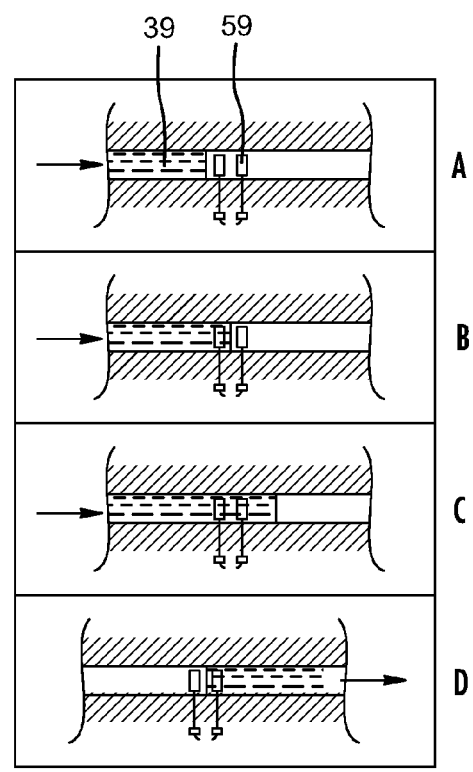
FIG. 14 is a cross-sectional illustration of the fluid flow across an electronic fluid sensor of the assay cartridge of FIG. 7, according to an exemplary embodiment.
Figure 13:
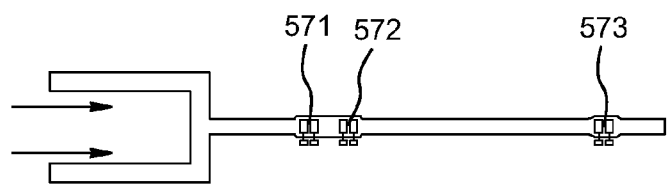
FIG. 13 is a linear representation of the fluid flow path through the assay cartridge of FIG. 7.

Referring now to FIGS. 13-14, the function of the electronic fluid sensors 57 is shown. FIG. 13 shows a linear representation of the fluid flow path through the assay cartridge 20. The fluid flows through the fluid channel 32 and over the multiple sensors 57. The sensors 57 are located within the testing portion 42 and are configured to facilitate the accurate dispensing of predetermined volumes of fluid into the fluid channel 32. The electronic fluid sensors 57 include conductance poles 59 that are configured to detect high or low impedance (i.e. whether fluid is flowing over the sensor). Prior to the flow of fluid through the fluid channel 32, the two poles 59 of a first electronic sensor 571 are in a high impedance "off" state (see fluid state A of FIG. 14). As fluid flows over the electronic sensor 571, the impedance remains high until the space between the two poles 59 is filled with fluid and fluid covers both poles 59 of the first sensor 571. At that point, the sensor 571 is in a low impedance "on" state (see fluid state B of FIG. 14). In the illustrated embodiment of FIG. 12, the assay cartridge 20 includes a second electronic sensor 572 that is similar in function to the first electronic sensor 571. In other exemplary embodiments, the assay cartridge 20 may include any number of electronic sensors 57, as is necessary for the particular application.

Figure 44:
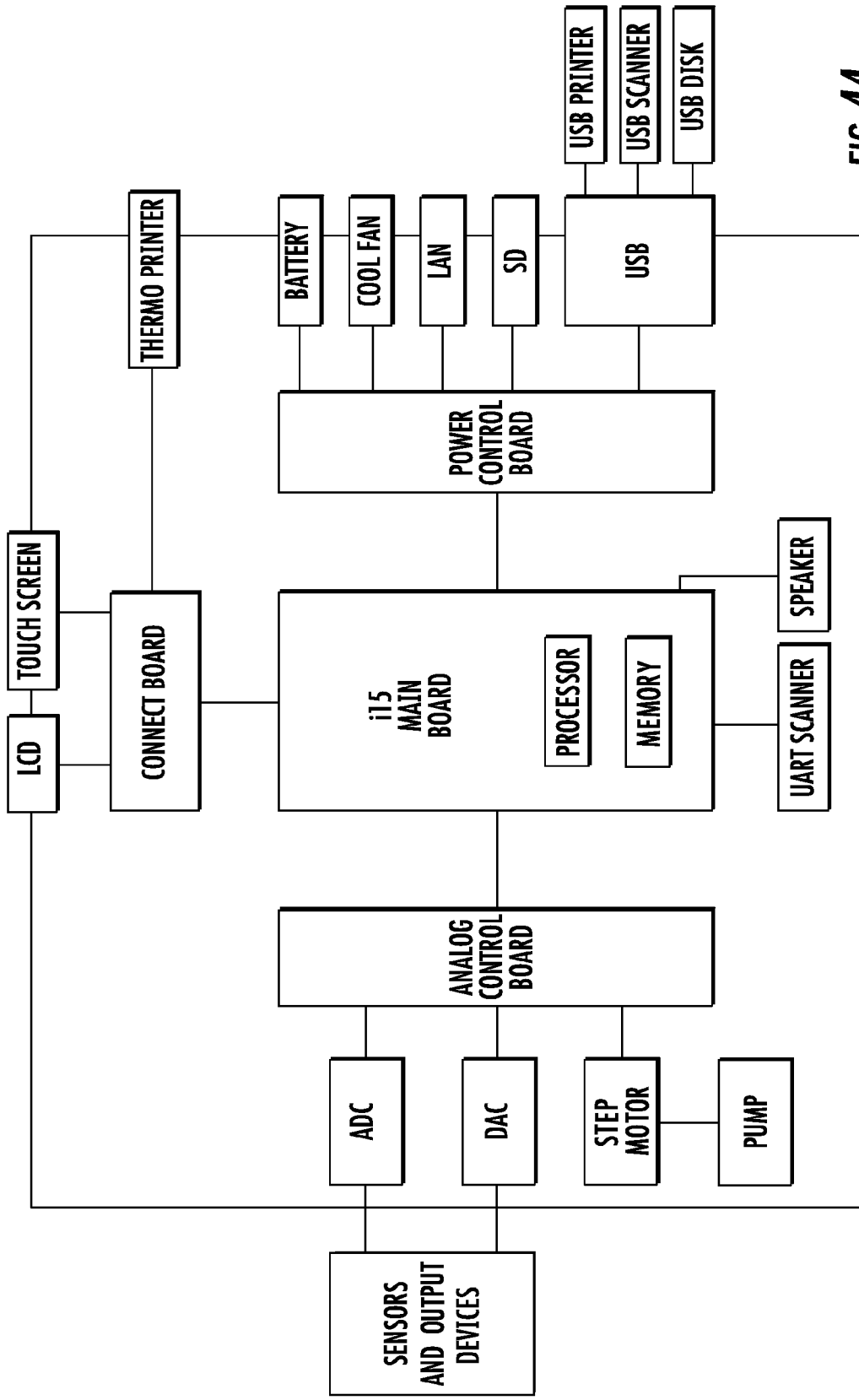
FIG. 44 is a diagram of a hardware organization for an in vitro medical diagnostic device, according to an exemplary embodiment.

In exemplary embodiments, the diagnostic device 10 includes a main board (shown in FIG. 44). The main board is part of a processing circuit (i.e. processing electronics), having a processor and memory. The main board receives one or more signals from the sensors 57, and is configured to turn the vacuum pump 50 on or off depending on the signals received from the electronic sensors 57. In the illustrated embodiment of FIG. 12, the electronic sensors 571 and 572 are configured to control the volume of fluid introduced into the assay cartridge 20. For instance, once the sensor 571 is in the "on" state, the main board may send a signal to turn off the vacuum pump 50, eliminating the negative pressure in the fluid channel 32 and stopping the fluid from flowing. The assay cartridge 20 may include any number of electronic sensors 57 configured to control the volume of fluid within the cartridge 20. The sensors 57 may be positioned at different points on the fluid flow path (e.g. within the testing portion 42, within the waste area 35, etc.), controlling the volume of fluid within the cartridge 20 according to what is suitable for the particular application.

Referring still to FIGS. 13-14, the assay cartridge 20 may also include an overflow prevention sensor 573, in exemplary embodiments. The overflow prevention sensor 573 has two poles 59 that are configured to detect high or low impedance. When the overflow prevention sensor 573 detects low impedance between its two poles 59, the main board may send a signal to the vacuum pump 50 (or to a controllable syringe 25, in an alternative embodiment) to immediately stop fluid flow to the channel 32. In exemplary embodiments, the overflow prevention sensor 573 operates as an emergency stop, intended to be used only when there is a failure somewhere in the system. In these exemplary embodiments, sensors 571 and 572 are configured to help control the volume of fluid introduced into the cartridge 20. The sensors 571 and 572 may be configured to communicate with the main board when fluid reaches the sensors 571 and 572. The main board may then send a signal to turn off the vacuum pump, eliminating the negative pressure in the fluid channel 32 and stopping the fluid from flowing. The overflow prevention sensor 573 serves as a safety to stop the fluid flow and to prevent the cartridge 20 from overflowing. In other exemplary embodiments, the overflow prevention sensor 573 may provide a signal to the main board, stopping the calibration fluid from flowing out of the cartridge 20. Before the fluid sample 39 is sent into the testing portion 42 for testing, the calibration fluid is pushed into the waste area 35. The overflow prevention sensor 573 may help prevent the calibration fluid from flowing further than a predetermined point within the waste area 35 by providing a signal to the main board. In response to the signal from the overflow prevention sensor 573, the main board can send a signal to turn off the vacuum pump 50, eliminating the negative pressure in the cartridge 20 and stopping the fluid from flowing to the cartridge 20. Therefore, the overflow prevention sensor 573 is intended to ensure that no fluid sample 39 or other fluid can leak into the rest of the device 10. In other embodiments, the main board may send a signal to reverse the flow of the vacuum pump 50, pushing fluid back through the channel 32 and preventing fluid from overflowing the cartridge 20. The assay cartridge 20 may include any number of electronic sensors 57 configured to supply signals to the main board in order to prevent fluid overflow. For example, the assay cartridge 20 may include multiple overflow prevention sensors 573 staggered throughout the waste area 35, each sensor 573 configured to stop fluid flow when fluid reaches the sensor 573.

Figure 15:
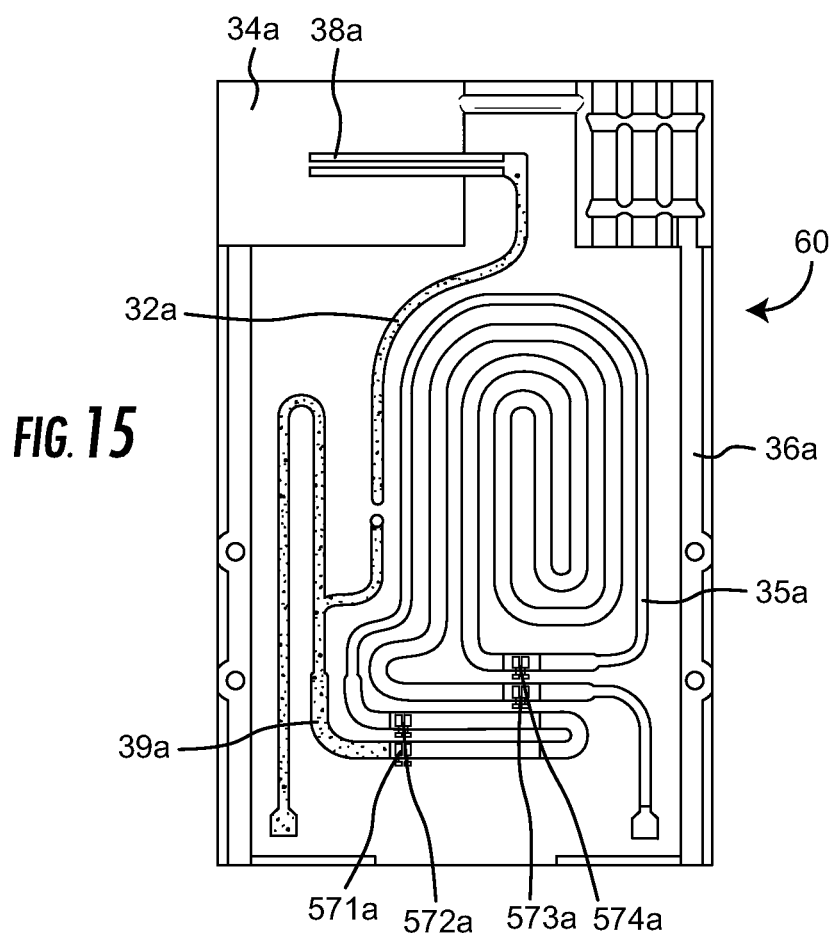
FIG. 15 is a back view of an assay cartridge, according to an alternative embodiment.

FIGS. 15-16 illustrate the alternative cartridge 60. In FIGS. 15-16, the placement of the electronic sensors 57a are shown, according to an alternative embodiment. In the illustrated embodiment of FIGS. 15-16, the assay cartridge 20 includes four electronic sensors 571a, 572a, 573a, and 574a. The electronic sensors 571a, 572a, and 573a are configured to allow a predetermined amount of fluid to enter the fluid channel 32a of the assay cartridge 60. FIG. 15 illustrates the assay cartridge 60 as fluid reaches the first electronic sensor 571a, while FIG. 16 illustrates the cartridge 60 as fluid reaches the overflow prevention sensor 573a. FIG. 17 shows a linear pathway where the fluid sample 39 can flow through the fluid channel 32a and over the sensors 57a, according to the alternative embodiment of FIGS. 15-16.

Figure 18:
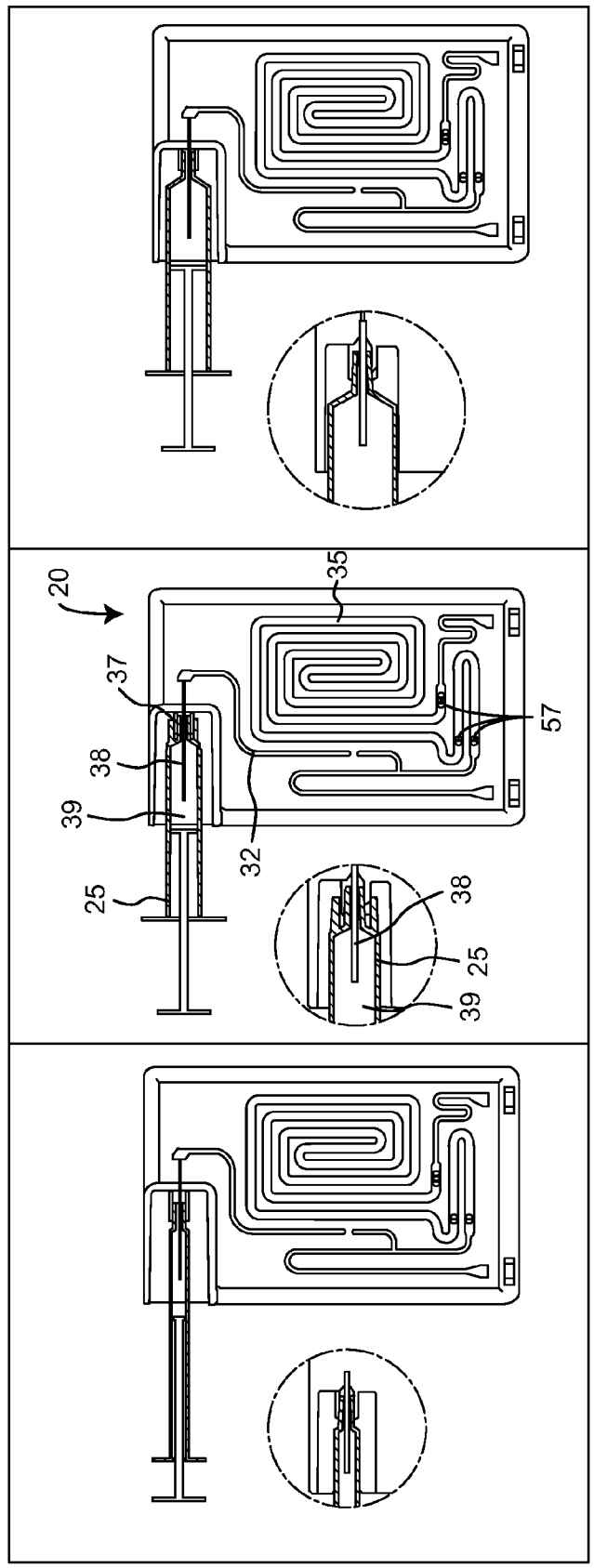
FIG. 18 is a cross-section view of a universal syringe interface, illustrating three different sized syringes, on an assay cartridge, according to an exemplary embodiment.

Referring now to FIG. 18, the receiver 34 of the assay cartridge 20 has a universal design, such that it is configured to receive more than one size receptacle (i.e. syringe 25). For example, the receiver 34 may receive a 1 ml, 3 ml, or a 5 ml syringe 25. However, in other exemplary embodiments, the receiver 34 may be sized differently or otherwise configured to receive any other size syringe 25. The syringe 25 may be inserted into the receiver 34. Once inside the receiver 34, the tip of the syringe 25 is fit into a C-shape structure 37, connecting with the interface 38. The fluid sample 39 is then aspirated into the interface 38. In exemplary embodiments, air flows through the C-shape structure 37 and into the area between the tip of the syringe 25 and the interface 38, replacing the sample 39 that is aspirated into the fluid channel 32. The receiver 34 may also be configured to receive a capillary tube (shown more particularly in FIG.

21). In exemplary embodiments, the interface 38 is adapted to mate with the receptacle (i.e. syringe 25, capillary tube, etc.) either directly or through an adapter.

Figure 19:
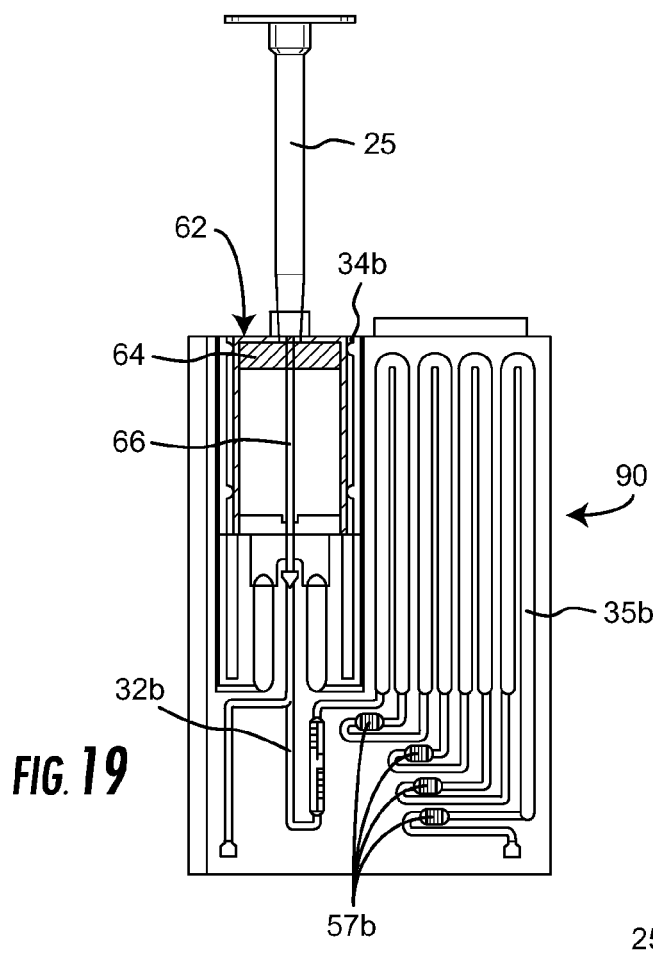
FIG. 19 is a front view of an assay cartridge with a syringe loaded from the top, according to an alternative embodiment.
Figure 20:
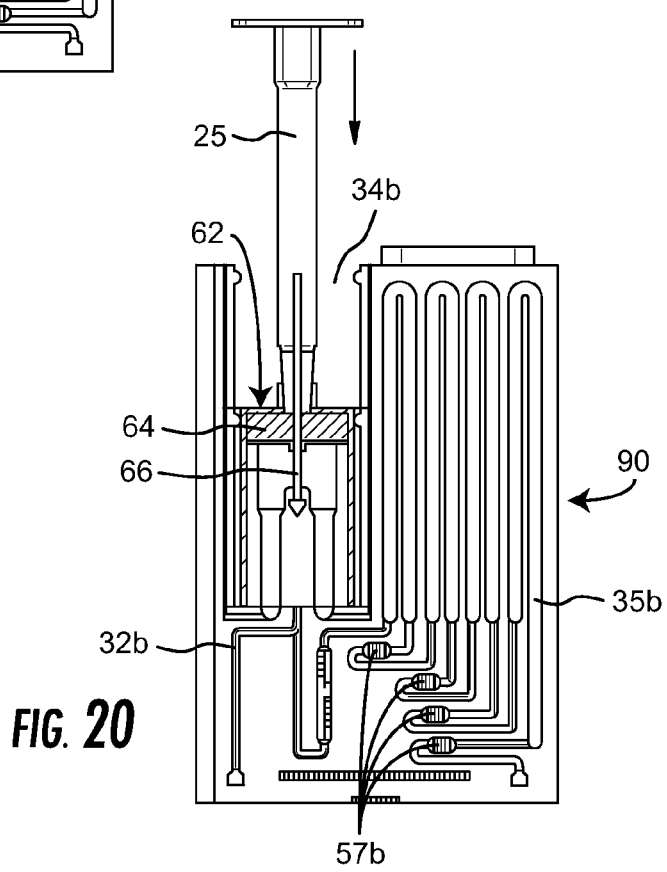
FIG. 20 is a front view of the assay cartridge of FIG. 19.

Referring to FIGS. 19-20, an alternative syringe configuration is shown, according to an exemplary embodiment. FIG. 19 is a front view of an assay cartridge 90 with a syringe 25 loaded from the top, according to an alternative embodiment. FIG. 20 is a front view of the assay cartridge 90 of FIG. 19. The alternative assay cartridge 90 includes a receiver 34b with an opening on the top of the cartridge 90. In this embodiment, the syringe 25 is introduced vertically, and connected to a slide 62. The cartridge 90 has a needle 66 attached to the end of the fluid channel 32b, which engages the end of the syringe 25. The cartridge 90 also includes a rubber seal ring 64 that seals the connection between the syringe 25 and the needle 66. In exemplary embodiments, the slide 62 moves vertically relative to the rest of the cartridge 90 when pressure is applied to the syringe 25 (shown in FIG. 20), and the needle 66 protrudes into the fluid sample 39. When the vacuum pump 50 is powered on, the fluid sample 39 from the syringe 25 flows into the fluid channel 32b.

Figure 21:
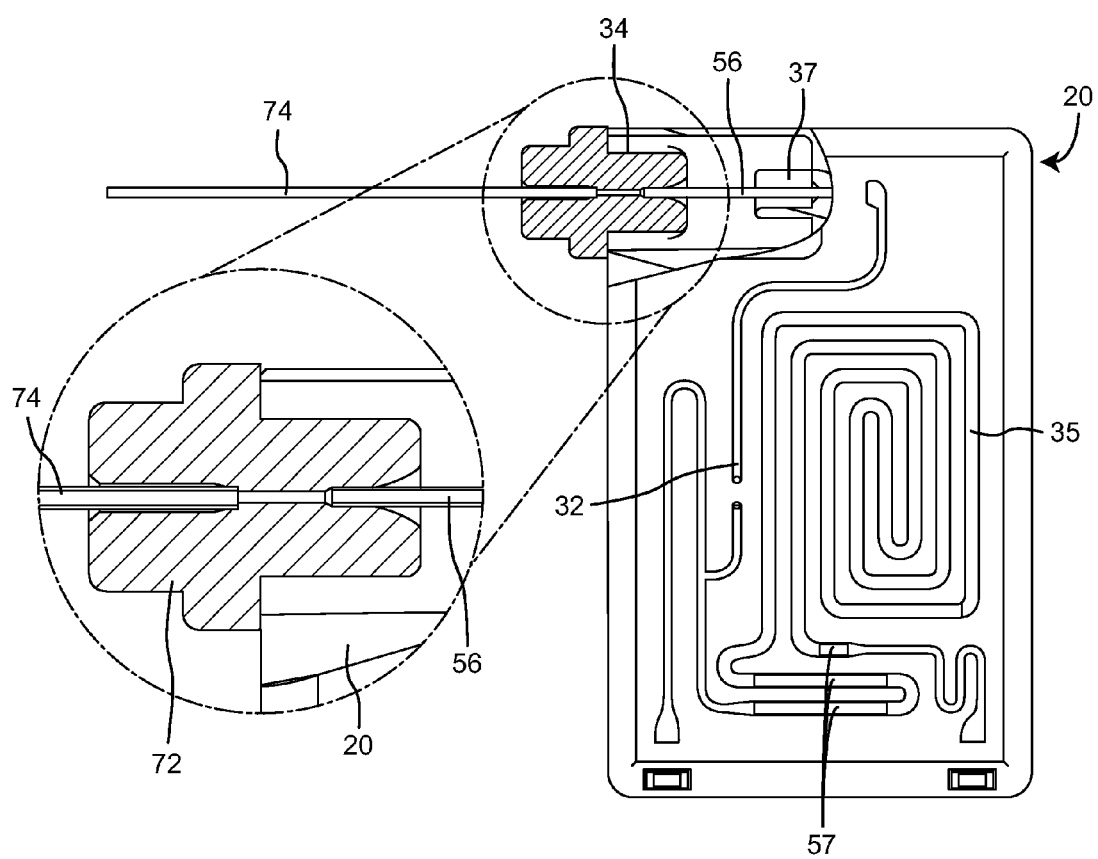
FIG. 21 is a back view of the assay cartridge of FIG. 1 with a capillary tube and capillary tube adapter coupled to the assay cartridge, according to an exemplary embodiment.
Figure 22:
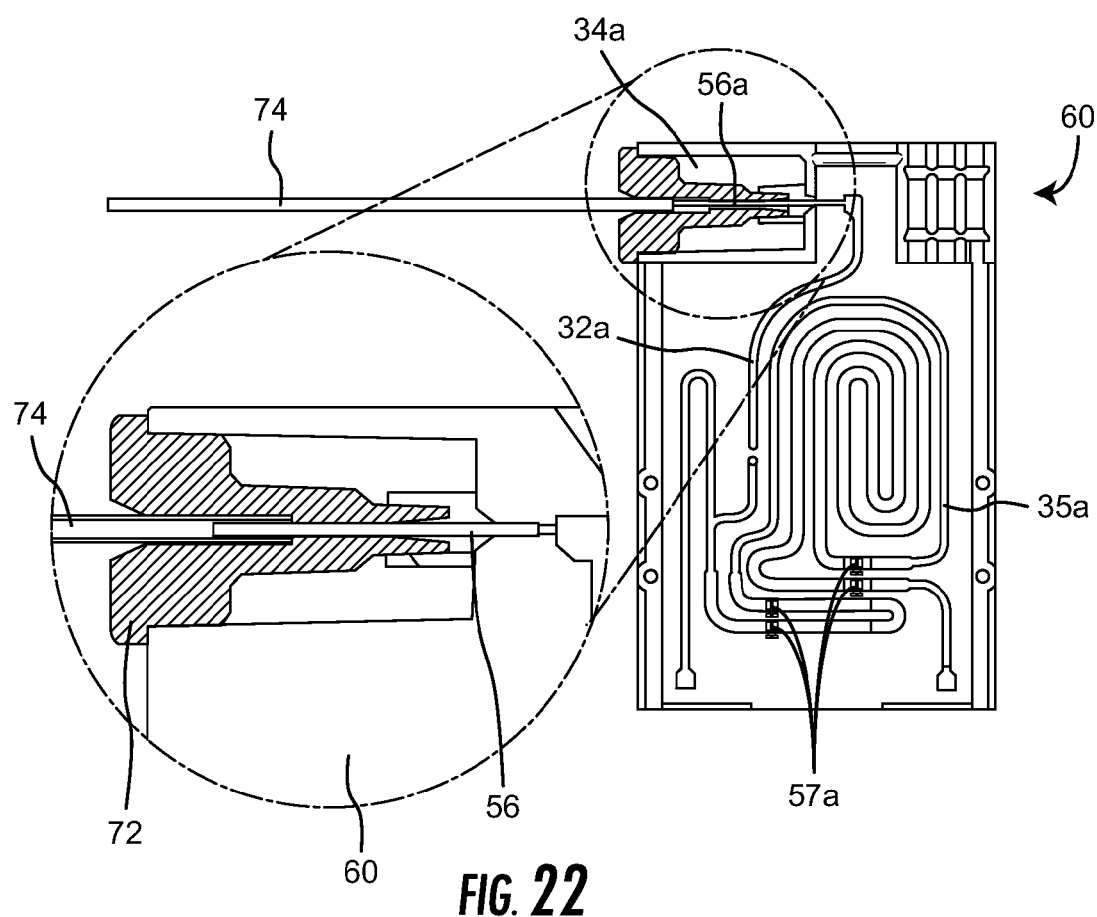
FIG. 22 is a back view of the assay cartridge of FIG. 15 with a capillary tube and capillary tube adapter coupled to the assay cartridge.

Referring now to FIGS. 21-22, a capillary tube is shown connected to the assay cartridge, according to exemplary embodiments. FIG. 21 is a back view of the assay cartridge 20 with the capillary tube 74 and capillary tube adapter 72 coupled to the assay cartridge 20, according to an exemplary embodiment. FIG. 22 is a back view of the assay cartridge 60 with the capillary tube 74 and capillary tube adapter 72 coupled to the assay cartridge 20, according to an exemplary embodiment. In these embodiments, a rubber or silicone capillary tube adapter 72 may be placed in the receiver 34 or 34a so that a small sample volume can be delivered with a capillary tube 74. One end of the capillary tube adapter 72 is connected with the capillary tube 74, and the other end is connected to the needle 56 or 56a in order to form a fluid path. The vacuum pump 50 may be powered on, producing a negative pressure in the assay cartridge 20 or 60, and forcing the fluid sample 39 to flow through the needle 56 and into the fluid channel 32 or 32a. Capillary tubes 74 may be used to test low volume fluid samples or used in other applications where capillary tubes 74 are used. The end wall of the inlet 34 has one or more holes configured to allow air to discharge when the capillary tube adapter 72 is plugged by the capillary tube 74 (i.e. does not allow fluid to pass).

Figure 23:
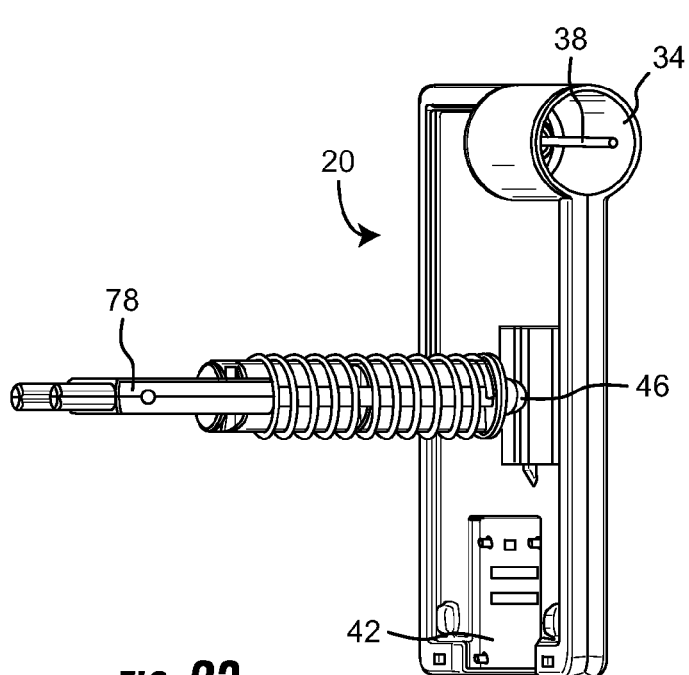
FIG. 23 is a perspective view of an assay cartridge, including a valve actuator actuating a pinch valve on the assay cartridge, according to an exemplary embodiment.
Figure 24:
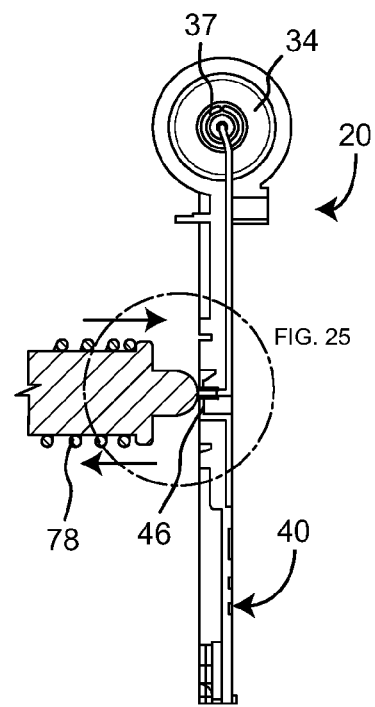
FIG. 24 is a cross-sectional side view of the assay cartridge of FIG. 23, including a valve actuator actuating a pinch valve on the assay cartridge, according to an exemplary embodiment.
Figure 25:
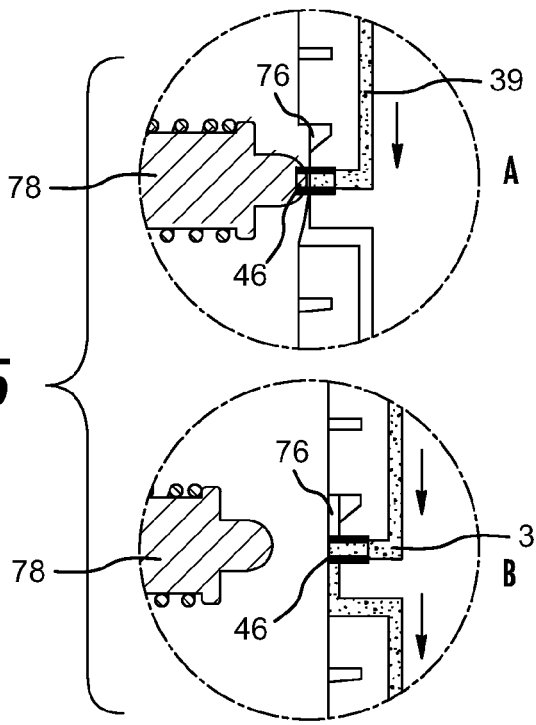
FIG. 25 is a cross-sectional illustration of a pinch valve in the closed and open position, according to an exemplary embodiment.

Referring now to FIGS. 23-25, a pinch valve 46 and related pinch valve actuator 78 for controlling the movement of the fluid sample 39 (i.e. valve control mechanism) within an assay cartridge 20 is shown, according to an exemplary embodiment. The assay cartridge 20 includes a pinch valve 46 that opens and closes, controlling the movement of the fluid sample 39 into the fluid channel 32. A pinch valve actuator 78 within the device 10 may manipulate the pinch valve 46, pressing against the valve 46 and causing the valve 46 to controllably open or close. FIG. 24 illustrates how the pinch valve actuator 78 contacts the valve 46 in exemplary embodiments, closing the valve 46 by pushing against it, and opening the valve 46 by pulling away from the cartridge 20 and the valve 46. When the pinch valve 46 is closed, as in FIG. 25A, the fluid sample 39 is prevented from reaching the fluid channel 32 for testing. However, when the pinch valve 46 is open, as in FIG. 25B, the fluid sample 39 is allowed to enter the testing portion 42. In exemplary embodiments, the fluid sample 39 is pulled into the fluid channel 32 by negative pressure created by the vacuum pump 50.

Figure 26:
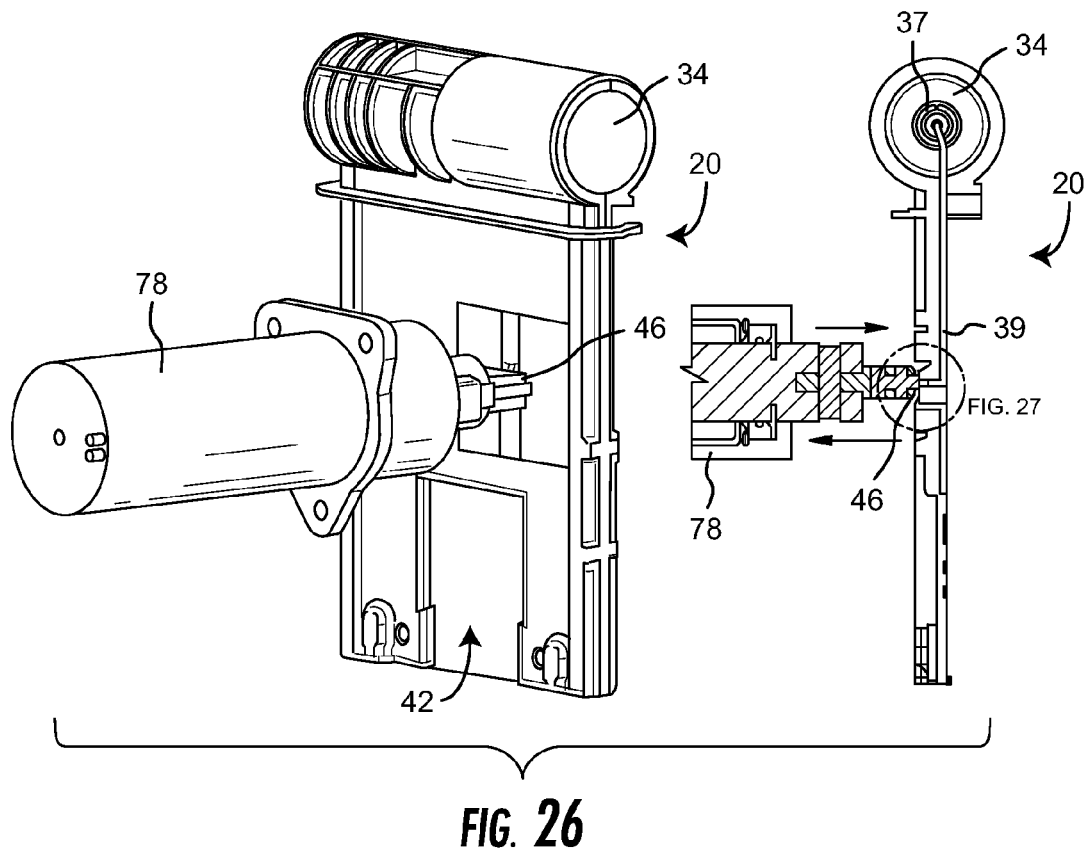
FIG. 26 is a perspective view and a cross-sectional side view of a pinch valve actuator actuating a pinch valve on an assay cartridge, according to an alternative embodiment.
Figure 27:
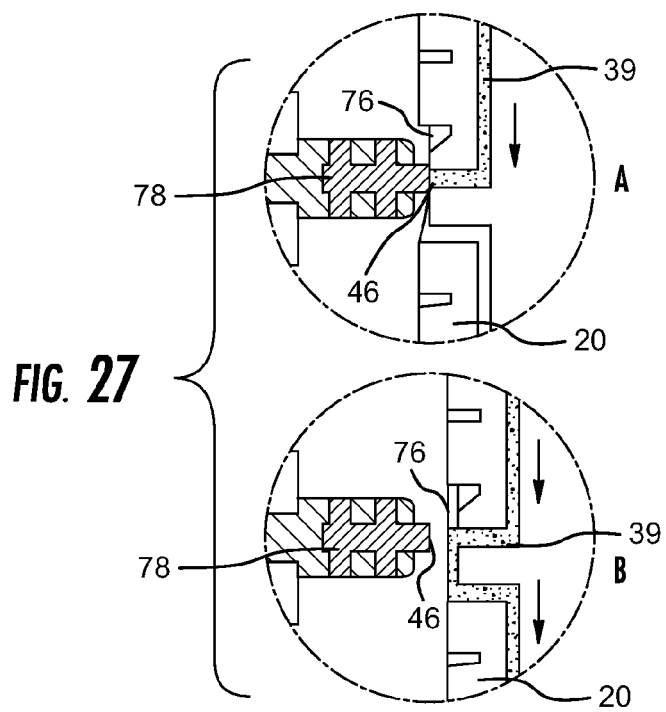
FIG. 27 is a cross-sectional illustration of a pinch valve in the closed and open position, according to an alternative embodiment.

FIG. 23 is a perspective view of the assay cartridge 20, including the valve actuator 78 engaging the pinch valve 46 on the assay cartridge 20, according to an exemplary embodiment. FIG. 24 is a cross-sectional side view of the assay cartridge 20 of FIG. 23, including the valve actuator 78 actuating the pinch valve 46 on the assay cartridge 20, according to an exemplary embodiment. FIG. 25 is a cross-sectional illustration of the pinch valve 46 in the closed and open position, according to an exemplary embodiment. FIGS. 26-27 illustrate the interaction between the pinch valve actuator 78 and the pinch valve 46, according to an alternative embodiment.

Figure 31:
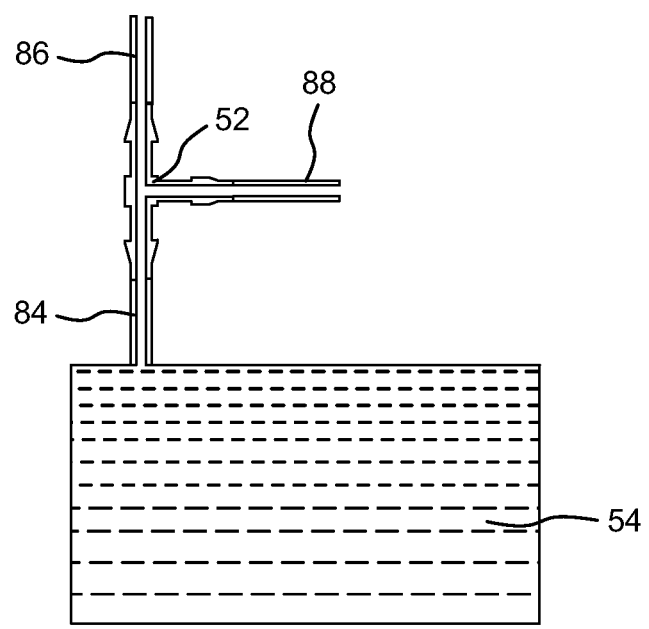
FIG. 31 is a cross-sectional illustration of the calibration cartridge of FIG. 28, including a T connector, and a fluid path and an air path from the calibration cartridge, according to an exemplary embodiment.

FIG. 28 is a perspective semi-transparent view of the calibration cartridge 30, according to an exemplary embodiment. FIG. 29 is a cross-sectional side view of the calibration cartridge 30 of FIG. 28, including a fluid pack 54, according to an exemplary embodiment. FIG. 30 is a close up cross-sectional view of a rod valve 83 of the calibration cartridge 30 of FIG. 28, including the rod valve 83 in the open and closed position, according to an exemplary embodiment. FIG. 31 is a cross-sectional illustration of the calibration cartridge 30 of FIG. 28, including a T connector 52, and a fluid path and an air path from the calibration cartridge 30, according to an exemplary embodiment.

Referring now to FIGS. 28-31 in more detail, a calibration cartridge is shown, according to an exemplary embodiment. The calibration cartridge 30 is disposable and removable. The calibration cartridge 30 includes a housing 82 that is intended to protect a fluid pack 54. The housing 82 is made of plastic, in exemplary embodiments, but may be made of another material or set of materials. The calibration cartridge 30 may also include a calibration cartridge cover (not shown). The cover is connected to a front portion (according to FIG. 28) of the cartridge 30, in exemplary embodiments. The calibration cartridge cover is intended to protect the calibration cartridge 30 when the cartridge 30 is not in use (i.e. not inserted into the diagnostic device 10).

The fluid pack 54, or chamber, is fluidly connected to the T connector 52. The fluid pack 54 may be a soft, flexible fluid pouch filled with unused calibration fluid. The T connector 52 includes a fluid flow channel 84, or pipe. The fluid flow channel 84 is configured to receive calibration fluid from the fluid pack 54, and to provide calibration fluid to a fluid channel 88 connecting to the assay cartridge 20. In exemplary embodiments and when the calibration cartridge 30 is fluidly connected to the assay cartridge 20, the height of the fluid flow channel 84 is higher than the height of the pinch valve 46. The T connector 52 also includes an air flow channel 86 that connects the T connector 52 to atmospheric air (i.e. ambient air), enabling the T connector 52 to send the air to the assay cartridge 20 as necessary. The fluid flow channel 84 and the air flow channel 86 meet at the T connector 52, forming a junction. In exemplary embodiments, a the calibration cartridge 30 includes a cap to close both the air and fluid ports during transport and storage. The calibration cartridge 30 may also include an L-shaped connector 122 (shown further in FIGS. 53A-C), in exemplary embodiments. The L-shaped connector 122 is configured to fluidly connect the fluid pack 54 to the T connector 52, thus providing a fluid connection to the assay cartridge 20. The L-shaped connector 122 is described in further detail below.

In exemplary embodiments, the calibration fluid flows through the T connector 52 to the needle 56 of the calibration cartridge 30. In these embodiments, the needle 56 is inserted into the assay cartridge 20 and is configured to supply the assay cartridge 20 with calibration fluid. A rubber insert 61 provides a seal around the connection between the needle 56 and the assay cartridge 20, in exemplary embodiments. The flow of calibration fluid and atmospheric air is controlled by pinch valves 47 and 48, respectively. The pinch valve 47 is located at the fluid flow channel 84, and the pinch valve 48 is located at the air flow channel 86. The pinch valves 47 and 48 are configured to open and close, regulating the introduction of fluids and gases (e.g. atmospheric air, calibration fluid, etc.) to the assay cartridge 20. In exemplary embodiments, when the vacuum pump 50 is controllably powered, fluid or gas flows through channel 84 or 86, travels through the needle 56, and enters the assay cartridge 20. In some exemplary embodiments, the fluid channel 88 provides a mixture of fluid and gas into the assay cartridge 20. In other exemplary embodiments, the fluid channel 88 provides either a fluid or a gas to the assay cartridge 20. The calibration cartridge 30 may introduce an air bubble to displace at least a portion of any calibration fluid previously introduced into the calibration fluid channel 88.

Referring still to FIG. 30, a rod valve of the calibration cartridge is shown, according to an exemplary embodiment. The calibration cartridge includes a rod valve 83, which moves between an open and closed position. During production, transport, and storage, the rod valve 83 may remain in the closed position, as in FIG. 30A. When in the closed position, the rod valve 83 is caused to press tightly against the fluid flow channel 84 (e.g. via a spring bias), sealing the calibration fluid in the fluid pack 54 from flowing to the needle 56 prior to engagement with the assay cartridge 20. In FIG. 30B, the rod valve 83 is in the open position. The rod valve 83 is in the open position after the calibration cartridge 30 has been installed to the diagnostic device 10. Calibration fluid may then be drawn into the assay cartridge 20. When the fluid pack 54 is engaged with the assay cartridge 20, the rod valve 83 is removed and in the open position, but the calibration fluid does not flow because the pinch valve 47 maintains a seal by pinching the T connector 52.

Figures 32, 33:
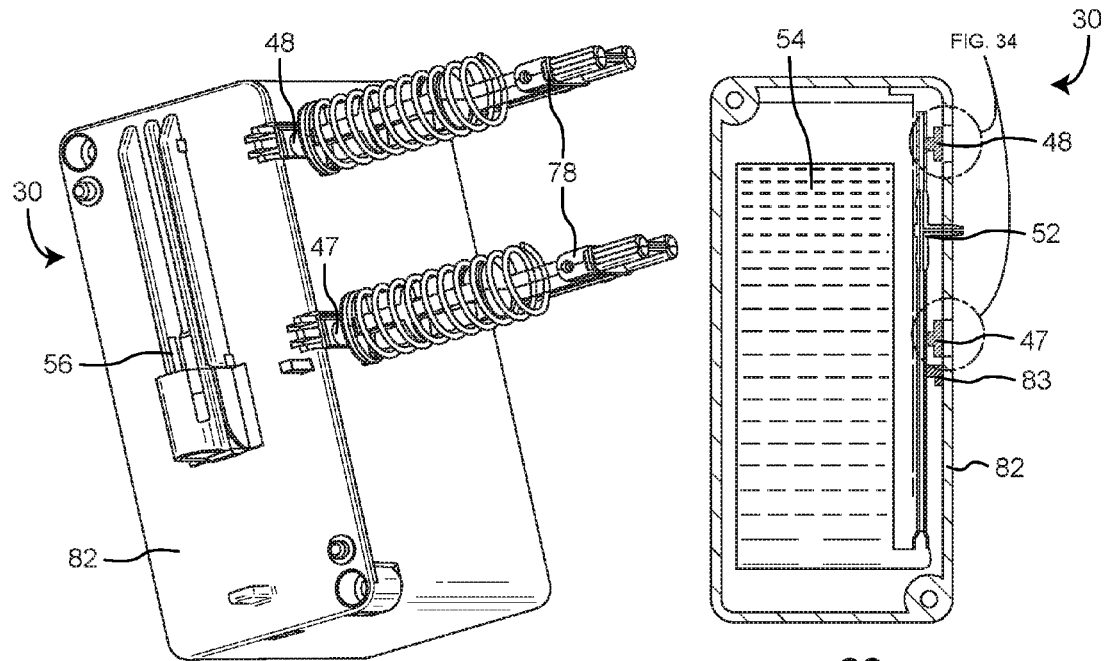
FIG. 32 is a perspective view of a calibration cartridge and two pinch valve actuators, according to an exemplary embodiment.
FIG. 33 is a cross-sectional side view of the calibration cartridge of FIG. 32, including a fluid pack, according to an exemplary embodiment.
Figure 34:
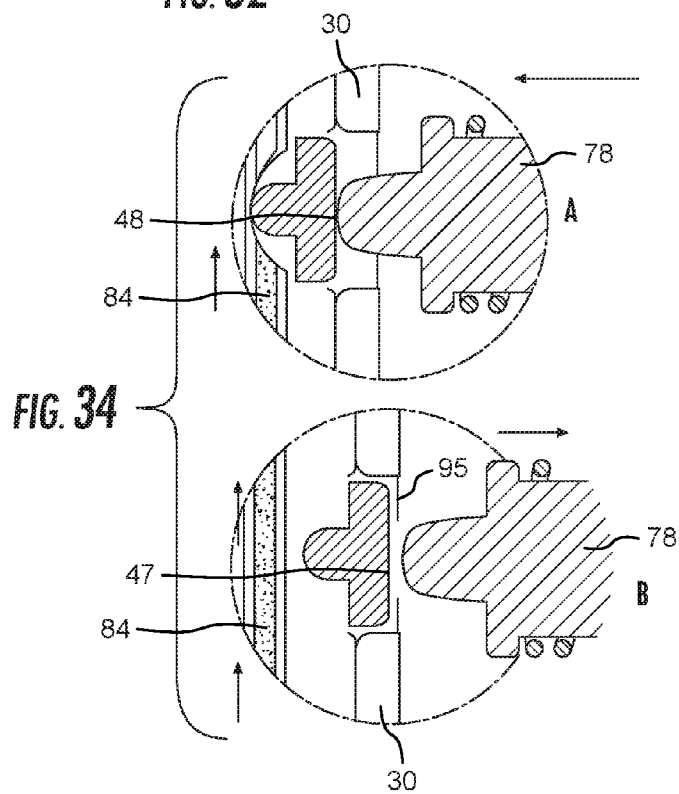
FIG. 34 is a cross-sectional view of a calibration cartridge pinch valve in the open and closed positions, according to an exemplary embodiment.

Referring now to FIGS. 32-34, the pinch valves 47 and 48 are aligned to the calibration fluid flow channel 84 and the air flow channel 86, respectively. The pinch valve actuators 78 are configured to push up against the pinch valves 47 and 48 on the calibration cartridge 30, closing the pinch valves 47 and 48 to prevent fluid or air from leaving the T connector 52. FIG. 33 shows the location of the pinch valves 47 and 48 on the calibration cartridge 30. The pinch valves 48 and 47 are aligned to pinch the fluid pathways for air and calibration fluid, respectively, in exemplary embodiments. FIGS. 34A-B show a cross-section of the pinch valves 47 and 48 in the closed position (FIG. 34A), and in the open position (FIG. 34B). FIG. 32 is a perspective view of the calibration cartridge 30 and two pinch valve actuators 78, according to an exemplary embodiment. FIG. 33 is a cross-sectional side view of the calibration cartridge 30, including a fluid pack 54. FIG. 34 is a cross-section view of a calibration cartridge pinch valve 47 or 48 in the open and closed positions, according to an exemplary embodiment.

Figure 37:
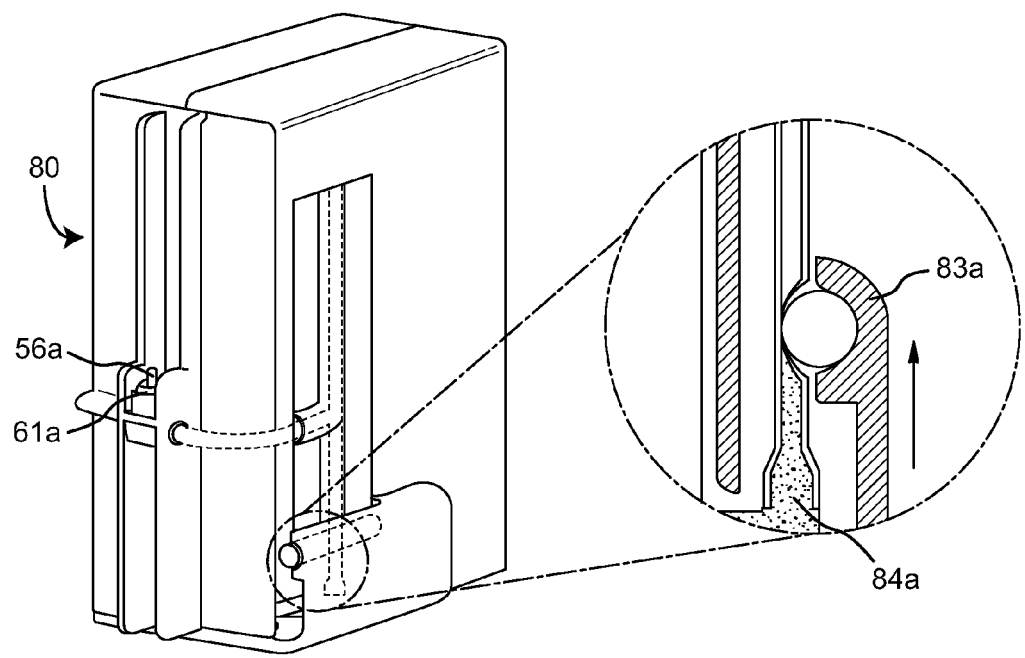
FIG. 37 is a perspective view of the calibration cartridge of FIG. 35 and a cross-sectional view of the calibration cartridge showing a rod valve in the closed position.
Figure 38:
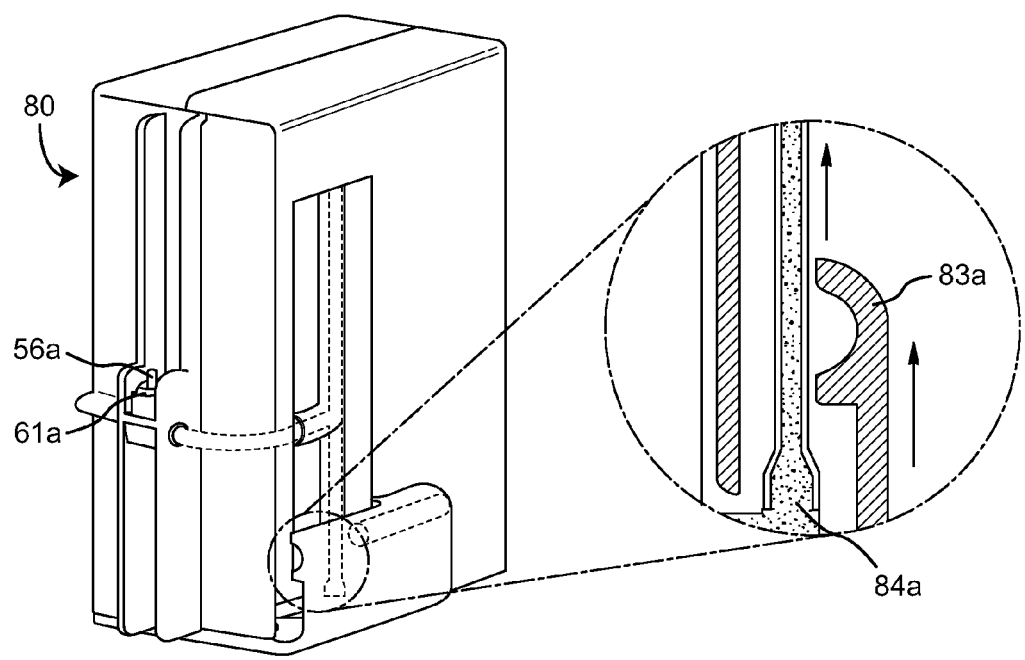
FIG. 38 is another perspective view of the calibration cartridge of FIG. 35 and a cross-sectional view of the calibration cartridge showing a rod valve in the open position.

FIG. 35 is a perspective and semi-transparent view of a calibration cartridge 80, according to an alternative embodiment. FIG. 36 is a cross-sectional view of the alternative calibration cartridge 80, including a fluid pack 54a and the T connector 52. FIG. 37 is a perspective view of the alternative calibration cartridge 80 and a cross-sectional view of the alternative calibration cartridge 80 showing the rod valve 83a in the closed position. FIG. 38 is another perspective view of the alternative calibration cartridge 80 and a cross-sectional view of the alternative calibration cartridge 80 showing the rod valve 83a in the open position.

Referring now to FIGS. 35-36, the alternative calibration cartridge 80 is shown. The alternative calibration cartridge 80 has a alternative rod valve 83a, which is shown more particularly in FIGS. 37-38. In the illustrated embodiment of FIG. 37, the rod valve 83a presses tightly against the channel 84a, preventing the fluid from flowing out of the channel 84a, and sealing the calibration fluid from flowing to the fluid output (i.e. the needle 56a). In order to allow calibration fluid flow, the rod valve 83a is caused to disengage. Once the calibration cartridge 80 is inserted into the device 10, for instance, the rod valve 83a is released so that the pressure is relieved and the flow is not restricted, allowing calibration fluid to flow out of the channel 84a. In FIG. 38, the rod valve 83a has been released, opening the channel 84a for calibration fluid to flow through. Once the calibration cartridge 30 has been removed from the device 10, the rod valve 83a is caused to return to the closed position (e.g. via a spring bias) to keep the remaining calibration fluid within the cartridge 80.

Referring now to FIGS. 39-41, the calibration cartridge 80 is shown according to an alternative embodiment. In FIGS. 39-41, pinch valve actuators 78a are shown as aligned with the pinch valves 47a and 48a. The pinch valve actuators 78a are configured to cause the pinch valves 47a and 48a to close by pinching respective portions of the fluid pathways 85a. The pinch valves 48a and 47a may include a flexible film area which may elastically press in toward the cartridge 80, closing the pinch valves 48a and 47a and restricting the flow of fluid and/or air. The pinch valves 48a and 47a are closed by pinch valve actuators 78a, in exemplary embodiments. FIG. 39 is another perspective view of the alternative calibration cartridge 80, showing pinch valve actuators 78a engaging the pinch valves 48a and 47a of the calibration cartridge 80 to regulate fluid and/or gas flow. FIG. 40 is a cross sectional view of the calibration cartridge 80, including pinch valves actuators engaging the pinch valves 48a and 47a of the calibration cartridge 80. The pinch valves 48a and 47a include rubber spacers 96 configured to create a fluid pathway 85a. FIG. 41 is a close up cross-sectional view of the pinch valve 47a for the fluid path in the open and closed positions, and a cross section view of the T connector 52 forming a fluid pathway with the rubber spacers 96.

FIG. 39 is another perspective view of the calibration cartridge 80, showing pinch valve actuators 78a engaging the pinch valves 48a and 47a of the calibration cartridge 80 to regulate fluid and/or gas flow, according to an exemplary embodiment. FIG. 40 is a cross-sectional view of the calibration cartridge 80, including pinch valve actuators 78a engaging the pinch valves 48a and 47a of the calibration cartridge 80. FIGS. 41A-B are close up cross-sectional views of a calibration cartridge pinch valve 48a or 47a in the closed and open positions, respectively, according to an exemplary embodiment.

Figure 42:
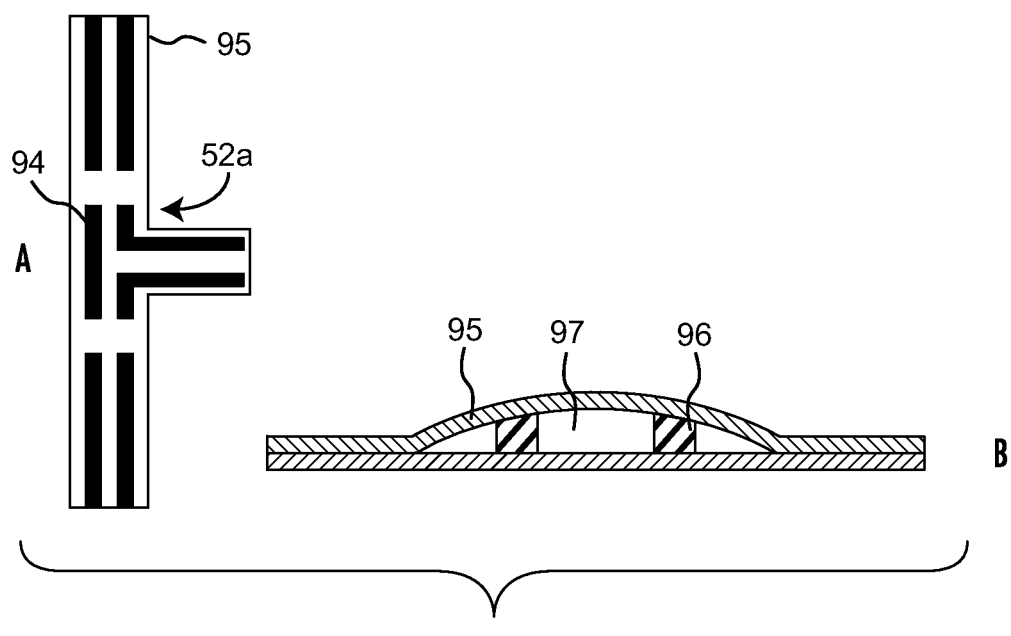
FIG. 42 is a close up cross-section view of a fluid pathway for a calibration cartridge, including a thin film formed over two rubber spacers, according to an exemplary embodiment.
Figure 43:
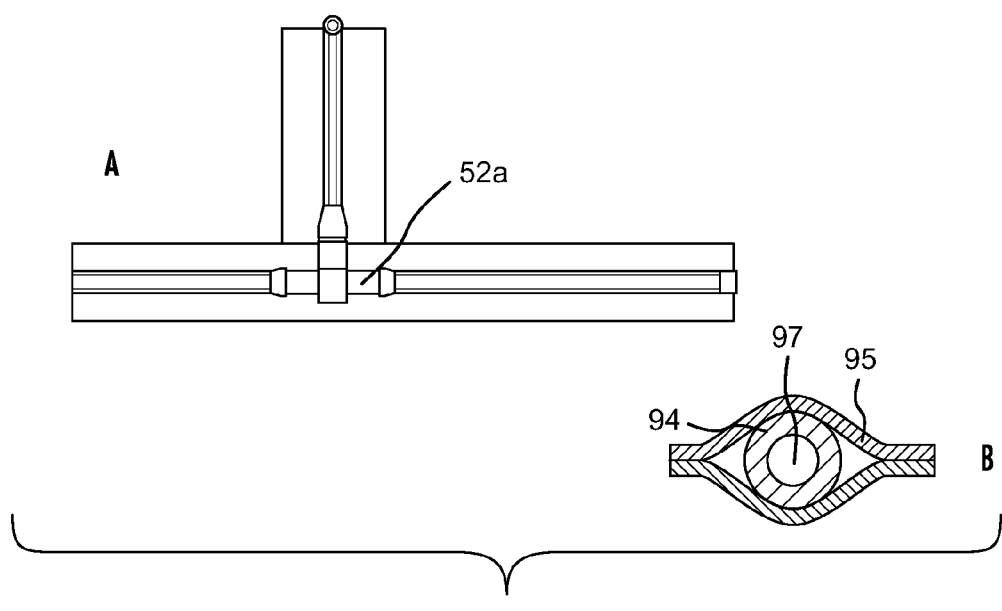
FIG. 43 is a close up cross-section view of the fluid pathway of FIG. 42, including the T connector.

Referring now to FIGS. 42-43, an alternative embodiment of the T connector 52 is shown. FIG. 42 is a close up cross-section view of a fluid pathway for the calibration cartridge 30, including a thin film formed over two rubber spacers 96, according to an exemplary embodiment. FIG. 43 is a close up cross-section view of a fluid pathway formed with a thin film 95 over an inserted tube. In this embodiment, the T connector 52 includes tubes 94 (shown in FIG. 43B) that are inserted between a thin film 95. FIG. 42B shows a cross-section of the T connector 52. Two rubber spacers 96 are sealed by the thin film 95, creating an air channel 97 within the T connector 52. In exemplary embodiments, the air channel 97 is made from dispensed silicon, but may be made from any other materials suitable for the application in other exemplary embodiments. The pinch valve may press tightly against the channel 97 in exemplary embodiments, regulating the opening and closing of the channel 97.

In the illustrated embodiment of FIGS. 42-43, the rubber spacers 96 are made from silicone and the thin film 95 is made of aluminum-plastic. However, in other exemplary embodiments, the rubber spacers 96 may be made of any other type of polymer or other suitable material, and the thin film 95 may be made of any material suitable for the particular application. The thin film 95 may be sealed over the rubber spacers 96 by "hot pressing," (a metallurgy process achieved by simultaneous application of heat and pressure) or by any other means suitable for sealing the air channel 97. In exemplary embodiments, the rubber spacers 96 have a concave dent configured to guide the needle 56 to pierce the thin film 95 rather than punch through the spacers 96.

Referring now to FIG. 44, a hardware organization diagram is shown for an in vitro medical diagnostic device 10, according to an exemplary embodiment. In exemplary embodiments, the ADC and DAC communicate with a plurality of electrochemical sensors 40 and with any other input or output devices, such as position sensors or heating elements 116. The electrochemical sensors 40 are located in the testing portion 42 of the assay cartridge 20. The sensors 40 are used by the processing electronics of the diagnostic device to interpret the chemical composition of the fluid within the testing portion 42. The ADC is configured to process analog signals from the electrochemical sensors 40. Once the ADC processes the output from the sensors 40, it may transmit the data to the analog control board. While the analog control board is named "analog control board" here and in the figures, it should be appreciated that the analog control board may include digital processing. The analog control board may utilize a DAC to convert digital outputs (on/off modulated signals) to analog signals (e.g., for the electrochemical sensors). For example, the DAC is used to control the applied potential for amperometric sensors.

Referring still to FIG. 44, each board shown (i.e., the connect board, the analog control board, the power control board, and the main board, etc.) may be implemented as a separate printed circuit board (PCB), integrated on the same PCB, or a combination of otherwise integrated and distributed. Each board may be considered processing electronics or a processing circuit. The processing electronics may include discrete components and/or integrated circuits. The power control board, for example, may include all discrete electronics components. Each board may include one or more processors. The processors may be variously implemented as general purpose processors, one or more application specific integrated circuit (ASIC), one or more field programmable gate arrays (FPGAs), a group of processing components, or other suitable electronic processing components. Each board may also include one or more memory devices. The memory of each board may be one or more devices (e.g., RAM, ROM, Flash memory, hard disk storage, etc.) for storing data and/or computer code for completing and/or facilitating the various processes described herein. The memory may be or include non-transient volatile memory and/or non-volatile memory. The memory may include database components, object code components, script components, or any other type of information structure for supporting the various activities and information structures described herein. The memory may be communicably connected to the processor and includes computer code modules for executing one or more processes described herein.

Referring still to FIG. 44, the analog control board can be coupled to more than one stepper motors. While one stepper motor is shown as coupled to the pump, another stepper motor may be coupled to a motor for a motor assembly 100 having a cam plate 102 (e.g., shown in FIGS. 46-52). The motor assembly 100 may be configured to control one or more valves 46-48, regulating the introduction of fluid into the assay cartridge 20. The motor assembly 100 is shown and further in FIGS. 46-52 and described further below. In yet other embodiments, the analog control board may be coupled to solenoids for control thereof. The main board may include a general purpose processor and memory. The memory of the main board may include a Linux environment or another operating system. The main board may variously trigger routines and other software existing on the analog control board. It should be noted that the analog control board may include its own operating system and software modules for conducting its activities as described herein.

Figure 45:
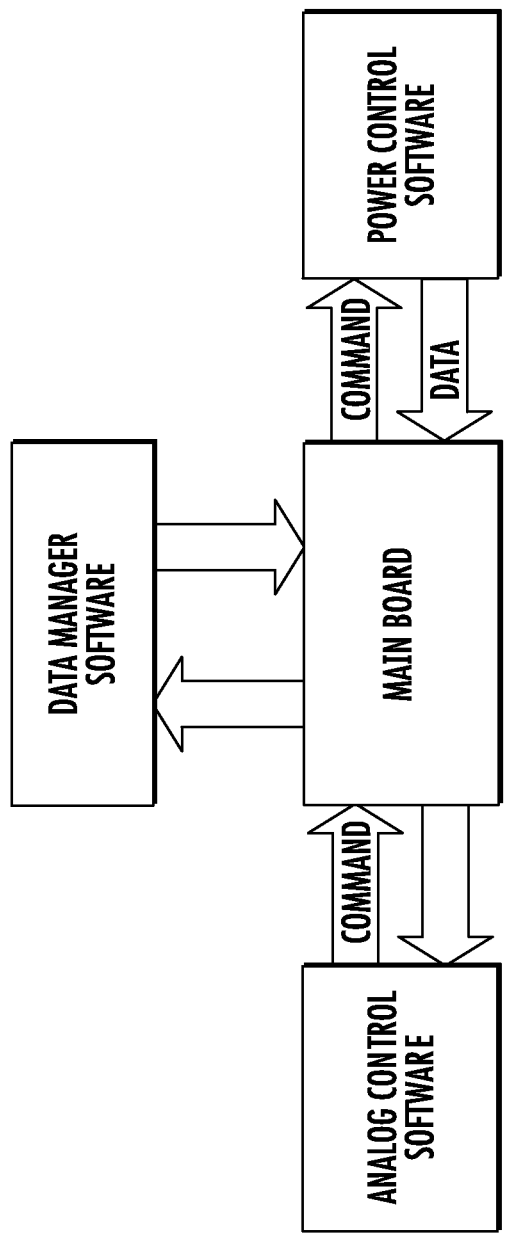
FIG. 45 is a diagram of a software organization for an in vitro medical diagnostic device, according to an exemplary embodiment.

The main board and the sub-boards may operate in concert as illustrated in FIG. 45. A data software manager may exist with the operating environment of the connect board. In other embodiments, the data manager may exist across the main board and the connect board. The analog control board may receive commands and function calls from the main board. The power control board may also receive commands and function calls from the main board. It should be noted that the power control board can control a variety of input and output activities beyond mere power supply management to the devices. For example, communications may be managed. The UART scanner may be a barcode scanner (e.g., 1D, 2D, etc.) as described herein. Data may be received at the main board from any of the sub-boards.

Figure 46:
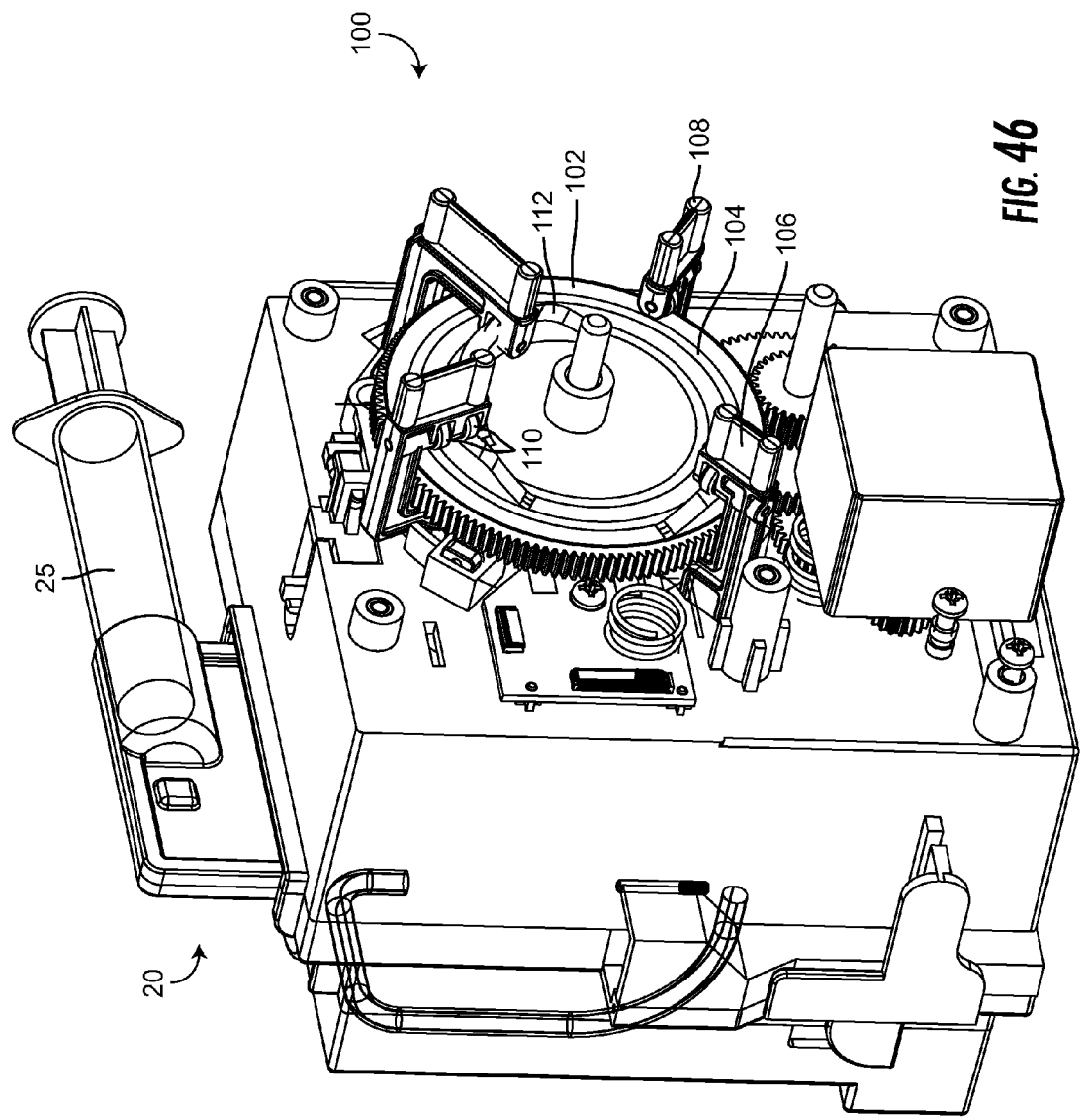
FIG. 46 is a perspective view of a motor assembly for controlling pinch valve actuators and heating elements for a diagnostic device, according to an exemplary embodiment.

Referring now to FIG. 46, a perspective view of a motor assembly 100 for controlling pinch valve actuators 78 is shown, according to an exemplary embodiment. The motor assembly 100 includes a cam plate 102. In exemplary embodiments, four plungers 108 and 106 (i.e. pinch valve actuators 78) are aligned with one or more pinch valves 46-48 or other valves. The plungers 108 and 106 are adjacent to and configured to receive the cam plate 102, resting on concentric circles 104 on the cam plate 102. Three plungers 108 are aligned with pinch valves 46-48 and are configured to open and close the pinch valves 46-48, depending on the stage of the device 10 in the testing sequence. The plungers 108 are pressed against the pinch valves 46-48, causing them to remain closed until the plungers 108 are actuated. A fourth plunger 106 is aligned with the pogo pins 114 (shown in FIG. 47) and heating elements 116 (i.e. heating plates or heating pads, shown in FIG. 47). The fourth plunger 106 is configured to cause the heating elements 116 to close over the testing portion 42 when the plunger 106 is actuated, heating the fluid (e.g. fluid sample 39) within the testing portion 42. The heating elements 116 are intended to cause a substantially constant temperature gradient to exist between two or more heating elements 116 on each side of the assay cartridge 20. The fourth plunger 106 is also configured to actuate the pogo pins 114, locking the assay cartridge 20 into a testing position.

The cam plate 102 is configured to rotate. As the cam plate 102 rotates, the plungers 108 and 106 "ride" along the concentric circles 104 of the cam plate 102 (i.e. make contact with the cam plate 102 as it rotates, rising and falling with the contours of the plate 102). Each of the concentric circles 104 has one or more raised portions 112. When one of the plungers 108 rides over one of the raised portions 112 of the concentric circle 104, the plunger 108 is pulled away from its associated pinch valve 46, 47, or 48, which will cause the associated valve 46, 47, or 48 to open.

Referring now to FIG. 47, a side view of the motor assembly 100 for controlling plungers 108 and 106 (i.e. pinch valve actuators) is shown, according to an exemplary embodiment. The heating elements 116 and the pogo pins 114 are associated with the fourth plunger 106. The fourth plunger 106 may actuate the heating elements 116 and pogo pins 114 when it rides over the raised portion 112 of the cam plate 102, causing the heating elements 116 to contact both sides of the testing portion 42. The fourth plunger may also cause the pogo pins 114 to contact the electrochemical sensors 57 of the cartridge 20. When the fourth plunger 106 is actuated by the cam plate 102, the plunger 106 causes the heating elements 116 to close on the assay cartridge 20, heating the fluid (e.g. fluid sample 39) within the testing portion 42.

Figure 48:
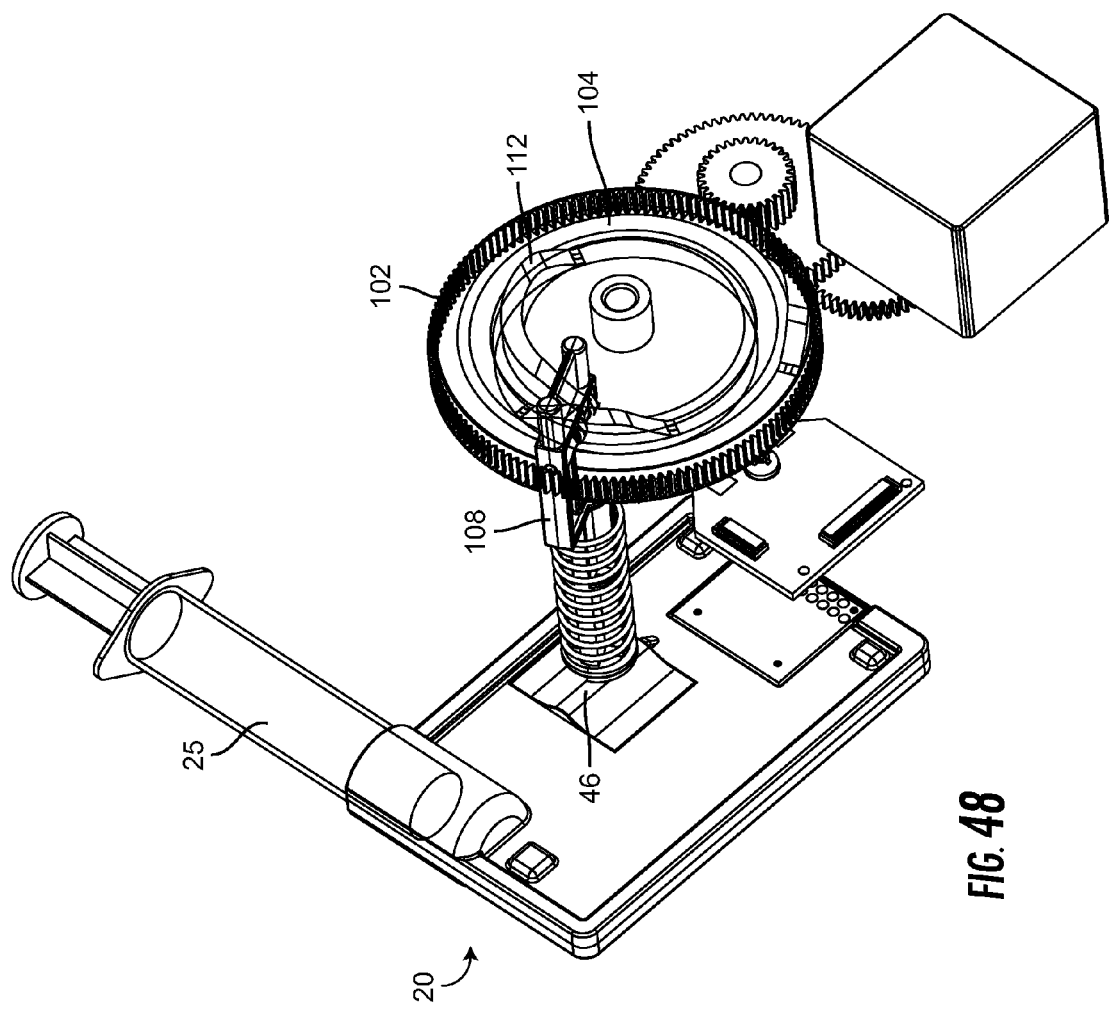
FIG. 48 is another perspective view of a motor for controlling pinch valve actuators for a diagnostic device, with the pinch valve actuator for an assay cartridge isolated in the illustration, according to an exemplary embodiment.

Referring now to FIG. 48, the plunger 108 associated with the pinch valve 46 for the assay cartridge 20 is isolated and shown, according to an exemplary embodiment. As the cam plate 102 rotates, the plunger 108 rides along one of the concentric circles 104 on the cam plate 102. When the device 10 is ready to test the fluid sample 39, the cam plate 102 rotates until the raised portion 112 of the concentric circle 104 comes in contact with the plunger 108. The plunger 108 is then forced by the raised portion 112 to pull away from the pinch valve 46, causing the pinch valve 46 to open, allowing the fluid sample 39 to travel to the testing portion 42.

Figure 49:
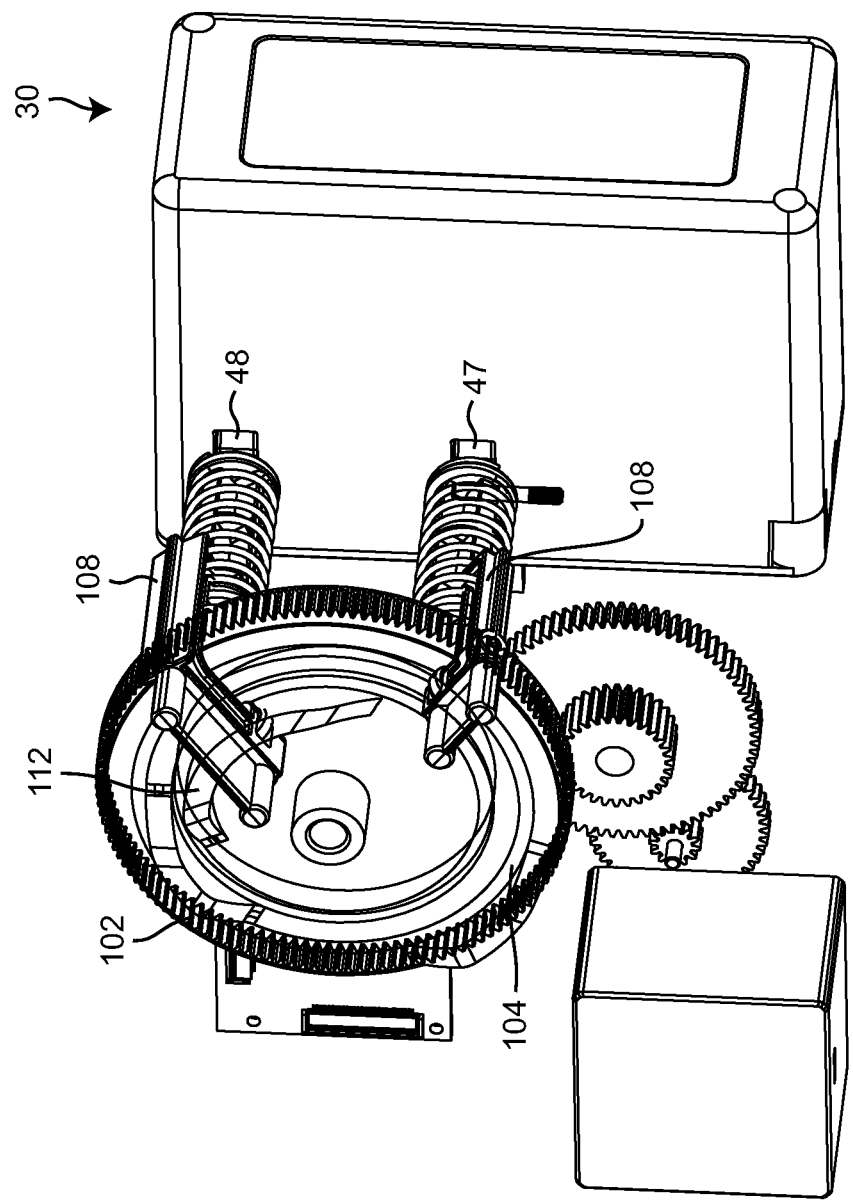
FIG. 49 is another perspective view of a motor for controlling pinch valve actuators for a diagnostic device, with the pinch valve actuators for a calibration cartridge isolated in the illustration, according to an exemplary embodiment.

Referring now to FIG. 49, the plungers 108 associated with the pinch valves 47 and 48 for the calibration fluid and air, respectively, are isolated and shown, according to an exemplary embodiment. As the cam plate 102 rotates, the plungers 108 ride along the concentric circles 104. The plungers 108 are pulled away from the pinch valves 47 and 48 as the cam plate 102 rotates to a predetermined position over the raised portions 112. The plungers 108 are pulled away from the pinch valves 47 and 48, causing the pinch valves 47 and 48 to open. Pinch valve 47 opens in order to send calibration fluid to the assay cartridge 20. Pinch valve 48 opens in order to send air into the assay cartridge 20.

Figure 50:
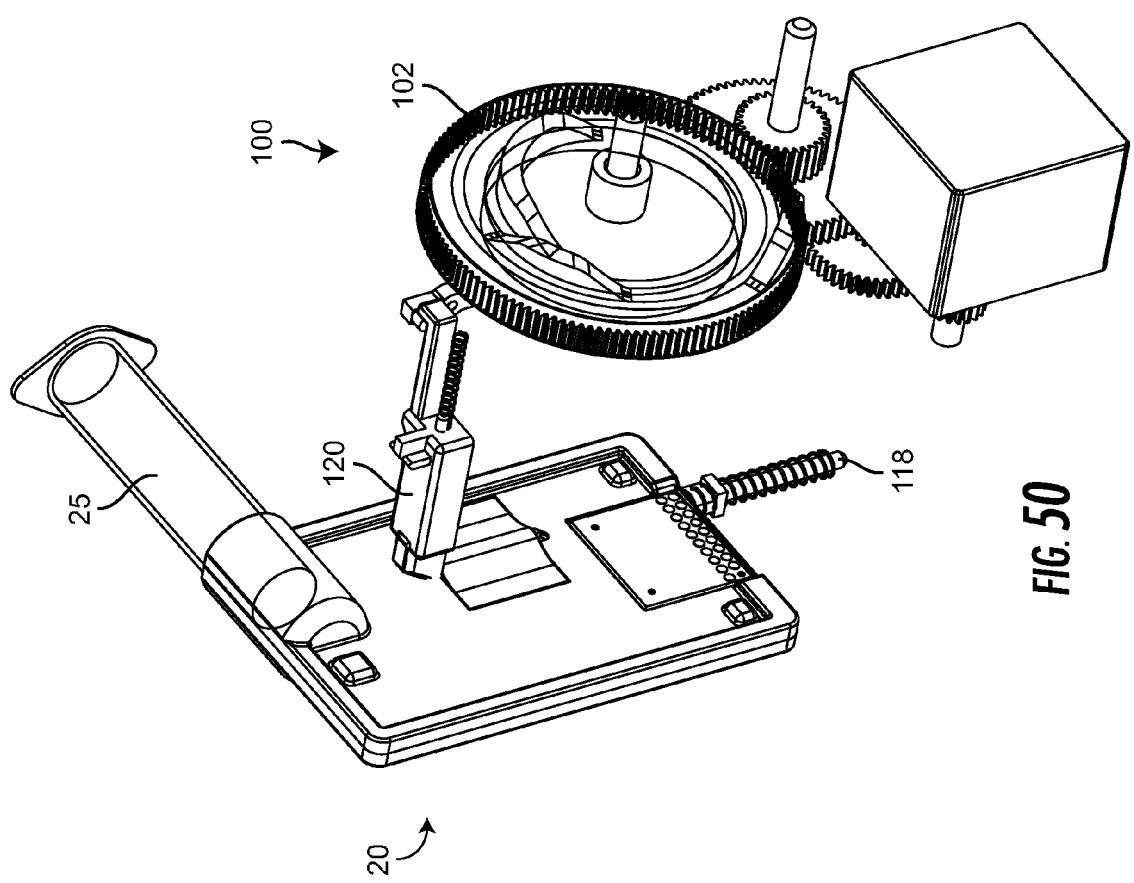
FIG. 50 is an isolated perspective view of a motor for actuating a pinch valve, including a pop up spring for ejecting the assay cartridge, and a locking rod for locking the assay cartridge within the diagnostic device, according to an exemplary embodiment.

Referring now to FIG. 50, an isolated view of a motor assembly 100 and a plunger 108 for actuating an assay cartridge pinch valve 46 are shown, according to an exemplary embodiment. An alternative embodiment of the plunger 108 is also shown in FIG. 56. In exemplary embodiments, the rotation of the cam plate 102 is also configured to eject the assay cartridge 20. The cam plate 102 is configured so that the plungers 108 and 106 are actuated in a sequence that matches the testing sequence of the device 10. The locking rod 120 locks the cartridge 20 when the cartridge 20 is inserted. At the end of the sequence, the cam plate 102 is configured to loosen the locking rod 120, releasing the cartridge 20. A pop up spring 118 at the bottom of the cartridge 20 pops up the cartridge 20, in exemplary embodiments, and is also used as a recognition mechanism for cartridge 20 insertion.

Figure 51:
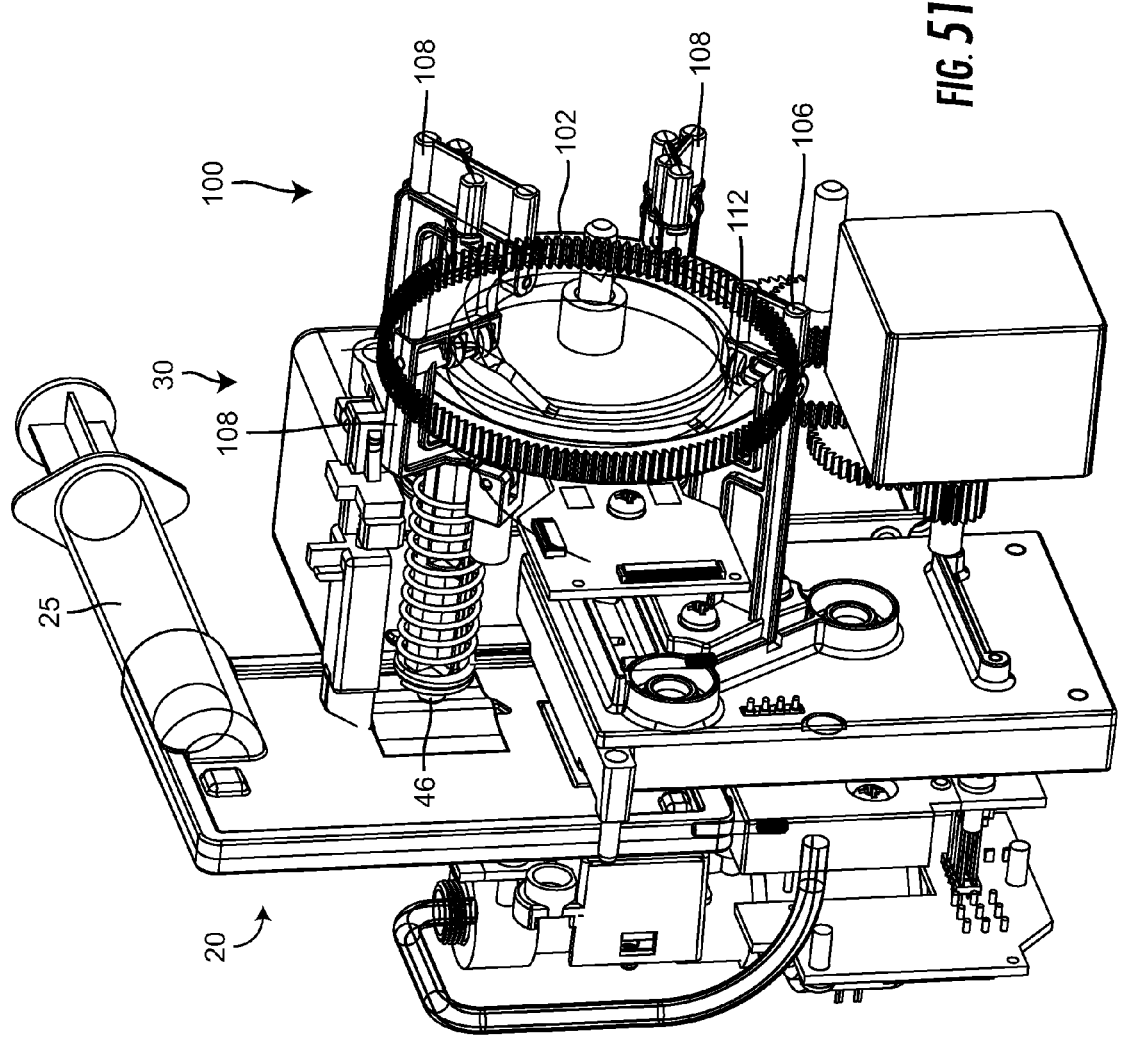
FIG. 51 is another perspective view of a motor for controlling pinch valve actuators for a diagnostic device, including the assay cartridge, calibration cartridge, syringe, and a portion of the diagnostic device, according to an exemplary embodiment.

Referring now to FIG. 51, a perspective view of a motor assembly 100 for controlling plungers 108 and 106 (i.e. pinch valve actuators) is shown, according to an exemplary embodiment.

Figure 52:
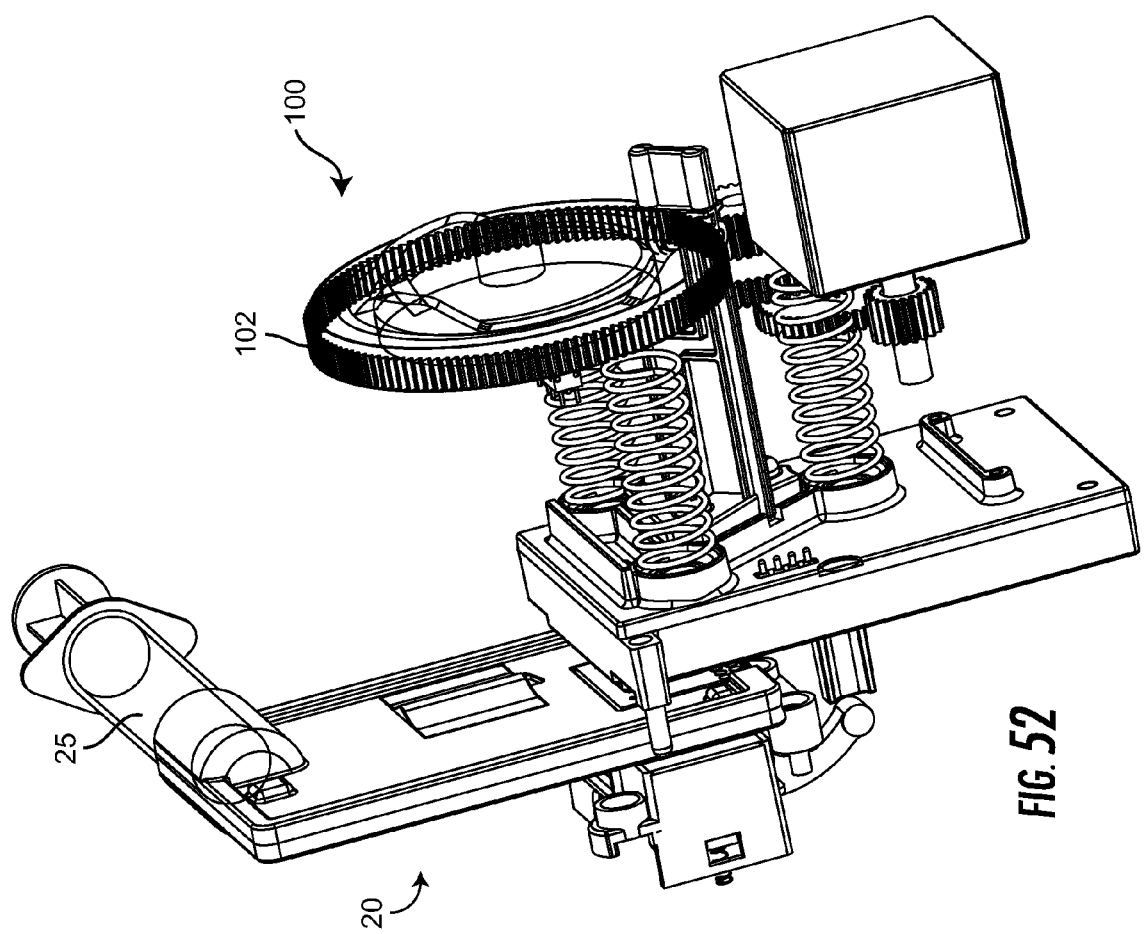
FIG. 52 is a perspective view of the motor embodiment of FIG. 47.

Referring now to FIG. 52, a perspective view of a motor assembly 100 for controlling plungers 108 and 106 (i.e. pinch valve actuators) is shown, according to an exemplary embodiment.

Figure 53C:
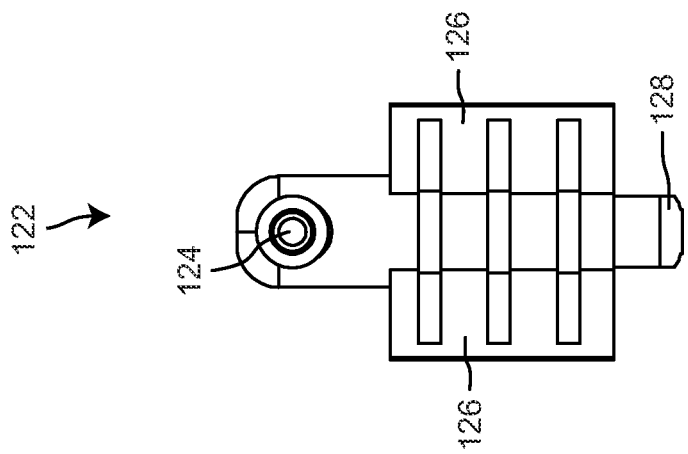
FIG. 53C is a front view of the L-shaped connector of FIG. 53A.
Figure 53B:
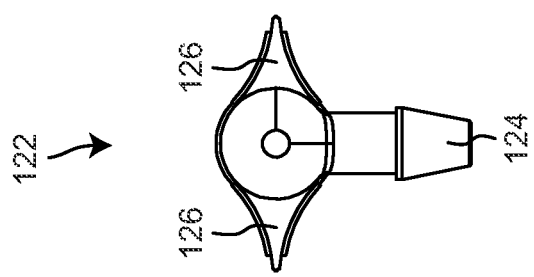
FIG. 53B is a back view of the L-shaped connector of FIG. 53A.
Figure 53A:
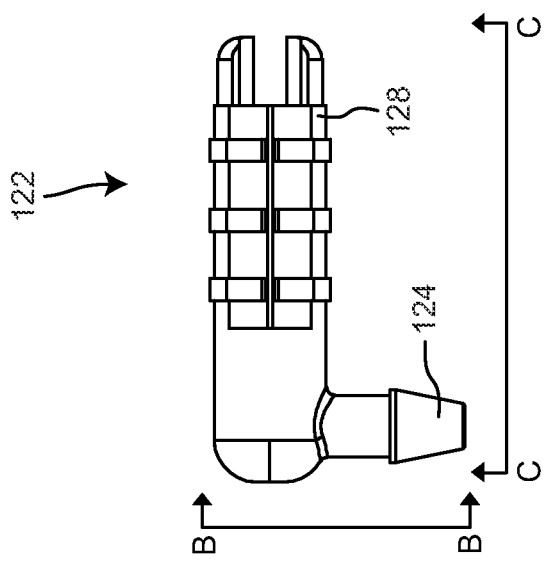
FIG. 53A is a side view of an L-shaped connector for providing calibration fluid from the fluid pack to the calibration cartridge, according to an exemplary embodiment.

Referring now to FIGS. 53A-C, an L-shaped connector for the calibration cartridge 30 is shown, according to an exemplary embodiment. The L-shaped connector 122 is connected to the bottom of the fluid pack 54 of the calibration cartridge 30, in exemplary embodiment. The L-shaped connector 122 is configured to deliver calibration fluid from the fluid pack 54. The L-shaped connector 122 includes a nozzle 124 configured to deliver calibration fluid. The L-shaped connector also includes a fluid pack end 128 that fluidly connects the L-shaped connector 122 to the fluid pack 54. The L-shaped connector 122 also includes one or more wings 126 extending out from the connector 122. The wings 126 are intended to allow fluid to travel through the L-shaped connector 122 when the pack is compressed.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

The construction and arrangement of the systems and methods for providing the calibration fluid cartridge and in vitro medical diagnostic device as shown in the various exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present invention as defined in the appended claims. The order or sequence of any process or method steps may be varied or re-sequenced according to alternative embodiments. Other substitutions, modifications, changes and omissions may be made in the design, operating conditions and arrangement of the various exemplary embodiments without departing from the scope of the present inventions.

The diagnostic device is generally shown to include a processing circuit including memory. The processing circuit may include a processor implemented as a general purpose processor, an application specific integrated circuit (ASIC), one or more field programmable gate arrays (FPGAs), a group of processing components, or other suitable electronic processing components. Memory is one or more devices (e.g., RAM, ROM, Flash memory, hard disk storage, etc.) for storing data and/or computer code for completing and/or facilitating the various processes described herein. Memory may be or include non-transient volatile memory or non-volatile memory. Memory may include database components, object code components, script components, or any other type of information structure for supporting the various activities and information structures described herein. Memory may be communicably connected to the processor and includes computer code modules for executing one or more processes described herein.

What is claimed is:

1. A calibration fluid cartridge for a diagnostic device, comprising:
    a chamber for holding unused calibration fluid;
    a flow channel configured to receive calibration fluid from the chamber and to provide calibration fluid to an output;
    a pinch valve moveable between an open position and a closed position and configured to control the flow of the calibration fluid through the fluid channel, wherein the pinch valve is configured to be actuated between the open position and the closed position by a pinch valve actuator subject to a spring bias pushing against the pinch valve, and wherein the calibration fluid cartridge does not carry the actuator;
    a rod valve moveable between an open position and a closed position, wherein when the rod valve is in the closed position, the rod valve is caused to provide a pressing force against the fluid flow channel, thereby deforming the fluid flow channel wall and sealing the calibration fluid from flowing to a fluid output;
    a housing containing the chamber and the flow channel, the housing partially containing the rod valve such that a portion of the rod valve protrudes from the housing; and
    a cap coupled to the housing, the cap configured to interface with the portion of the rod valve such that the rod valve is moved into the closed position when the cap for the calibration fluid cartridge is removed, prior to engagement with the diagnostic device;
    wherein the rod valve is biased to the open position when the calibration fluid cartridge is inserted into the diagnostic device; and
    wherein the rod valve is returned to the closed position when the calibration fluid cartridge is removed from the diagnostic device.

2. The calibration fluid cartridge of claim 1, further comprising:
    a junction for receiving gas in the flow channel; and
    a second pinch valve configured to control the flow of gas through the flow channel.

3. The calibration fluid cartridge of claim 2, further comprising:
    an ambient air channel that receives ambient air and provides the air to the junction for receiving gas in the flow channel.

4. The calibration fluid cartridge of claim 2 in which the pinch valves control the air flow and calibration fluid flow to the output.

5. The calibration fluid cartridge of claim 1, further comprising:
    an output needle and fluid conduit for communicating with a disposable assay cartridge.

6. The calibration fluid cartridge of claim 1 in which the output of the calibration fluid cartridge is located at the bottom of the calibration fluid container.

7. The calibration fluid cartridge of claim 1, further comprising an L shaped connector connected to the flow channel, the L-shaped connector positioned at the bottom of the calibration fluid cartridge and having one or more wings extending from the L-shaped connector and configured to maintain the flow of calibration fluid to the output.

8. A calibration fluid cartridge for a diagnostic device, comprising:
    a chamber for holding unused calibration fluid;
    a flow channel configured to receive calibration fluid from the chamber and to provide calibration fluid to an output;
    a junction for receiving gas in the flow channel;
    a system of valves such that gas and calibration fluid can controllably flow to the output;
    an ambient air channel that receives ambient air and provides the air to the junction for receiving gas in the flow channel;
    a first pinch valve for controlling the air flow to the output;
    a second pinch valve for controlling the calibration fluid flow to the output;
    a housing containing the chamber and the flow channel; and
    a cap coupled to the housing, the cap configured to cause the flow channel to close when the cap is coupled to the housing;
    wherein each pinch valve is actuated between an opened position and closed position by a pinch valve actuator pressing against the pinch valve; and
    wherein the pinch valve actuator is not carried by the calibration fluid cartridge.

9. The calibration fluid cartridge of claim 8 in which the pinch valves are closed under pressure and open in the absence of pressure, wherein the one or more actuators are controlled by processing electronics.

10. The calibration fluid cartridge of claim 8, further comprising:
    a rod valve that seals the calibration fluid from flowing to fluid output when the cap for the calibration fluid cartridge is removed, prior to engagement with the diagnostic device; wherein the rod valve is released once the calibration fluid cartridge is inserted into the diagnostic device; wherein the rod valve returns to the closed position again, to keep the remaining fluid inside cartridge, once it is disengaged with diagnostic device.

11. The calibration fluid cartridge of claim 8, further comprising:
    an output needle and fluid conduit for communicating with disposable assay cartridge.

12. The calibration fluid cartridge of claim 8 in which the output of the calibration fluid cartridge is located at the bottom of the calibration fluid container.

13. The calibration fluid cartridge of claim 8, further comprising an L shaped connector connected to the flow channel, the L-shaped connector positioned at the bottom of the calibration fluid cartridge and having one or more wings extending from an outlet of the connector and configured to protect the output from being blocked.

* * * * *